(12) United States Patent
Maldonado et al.

(10) Patent No.: US 11,376,343 B2
(45) Date of Patent: *Jul. 5, 2022

(54) ABSORBENT ARTICLE WITH GRAPHICS PRINTED IN PRESERVATIVE-FREE INK, AND METHODS OF MANUFACTURE THEREOF

(71) Applicant: The Procter & Gamble Company, Cincinnati, OH (US)

(72) Inventors: Clarissa Maldonado, Cincinnati, OH (US); Douglas E. Bugner, Rochester, NY (US); Wayne Cook, Xenia, OH (US); Allan Sowinski, Rochester, NY (US)

(73) Assignee: The Procter & Gamble Company, Cincinnati, OH (US)

( * ) Notice: Subject to any disclaimer, the term of this patent is extended or adjusted under 35 U.S.C. 154(b) by 782 days.

This patent is subject to a terminal disclaimer.

(21) Appl. No.: 16/216,083

(22) Filed: Dec. 11, 2018

(65) Prior Publication Data

US 2020/0129658 A1    Apr. 30, 2020

Related U.S. Application Data

(63) Continuation-in-part of application No. 16/171,433, filed on Oct. 26, 2018, now Pat. No. 11,185,452.

(51) Int. Cl.
*A61L 15/42* (2006.01)
*A61F 13/84* (2006.01)
(Continued)

(52) U.S. Cl.
CPC .......... *A61L 15/42* (2013.01); *A61F 13/8405* (2013.01); *A61L 15/20* (2013.01);
(Continued)

(58) Field of Classification Search
CPC .................. A61F 13/84; A61F 13/8405; A61F 2013/8497; A61L 15/20; A61L 15/42;
(Continued)

(56) References Cited

U.S. PATENT DOCUMENTS 3,911,173 A    10/1975    Sprague, Jr.
3,929,135 A    12/1975    Thompson
(Continued)

FOREIGN PATENT DOCUMENTS

EP         1013450 B1     7/2006
WO    WO2011103183 A1    8/2011

OTHER PUBLICATIONS

All Office Actions, U.S. Appl. No. 16/71433, See Pair.
(Continued)

*Primary Examiner* — Michele M Kidwell
(74) *Attorney, Agent, or Firm* — William E. Gallagher

(57) ABSTRACT

Absorbent articles having components bearing graphics printed using particular inkjet ink compositions and fluid sets are disclosed. The aqueous inkjet ink compositions may include a composition consisting of one or more compounds represented by the following Structure I:

HO—CH2-CH2-R        (I)

wherein R may be a substituted or unsubstituted phenyl group or a substituted or unsubstituted phenoxy group. Printed regions of components of the articles may bear deposits of dried ink including constituents of the disclosed compositions, that include the one or more Structure I compound(s). The presence of the Structure I compounds in the printed regions may have an effect of inhibiting bacterial growth thereon.

21 Claims, 3 Drawing Sheets

(51) Int. Cl.
*A61L 15/20* (2006.01)
*C09D 11/107* (2014.01)
*C09D 11/102* (2014.01)
*C09D 11/38* (2014.01)
*C09D 11/03* (2014.01)

(52) U.S. Cl.
CPC ............ *C09D 11/03* (2013.01); *C09D 11/102* (2013.01); *C09D 11/107* (2013.01); *C09D 11/38* (2013.01); *A61F 2013/8497* (2013.01)

(58) Field of Classification Search
CPC ......... A61L 15/46; A61L 15/56; C09D 11/03; C09D 11/107; C09D 11/322; C09D 11/38; C09D 11/54; D06P 5/30
See application file for complete search history.

(56) References Cited

U.S. PATENT DOCUMENTS

| | | | |
|---|---|---|---|
| 4,324,246 A | 4/1982 | Mullane et al. |
| 4,342,314 A | 8/1982 | Radel et al. |
| 4,463,045 A | 7/1984 | Ahr et al. |
| 4,573,986 A | 3/1986 | Minetola et al. |
| 4,785,996 A | 11/1988 | Ziecker et al. |
| 4,842,666 A | 6/1989 | Werenicz |
| 5,006,394 A | 4/1991 | Baird |
| 5,026,427 A | 6/1991 | Mitchell et al. |
| 5,141,556 A | 8/1992 | Matrick |
| 5,160,370 A | 11/1992 | Suga et al. |
| 5,169,436 A | 12/1992 | Matrick |
| 5,394,177 A | 2/1995 | McCann et al. |
| 6,079,821 A | 6/2000 | Chwalek et al. |
| 6,505,921 B2 | 1/2003 | Chwalek et al. |
| 6,517,197 B2 | 2/2003 | Hawkins et al. |
| 6,554,410 B2 | 4/2003 | Jeanmaire et al. |
| 6,575,566 B1 | 6/2003 | Jeanmaire et al. |
| 6,588,888 B2 | 7/2003 | Jeanmaire et al. |
| 6,682,182 B2 | 1/2004 | Jeanmaire et al. |
| 6,793,328 B2 | 9/2004 | Jeanmaire |
| 6,817,705 B1 | 11/2004 | Crockett et al. |
| 6,866,370 B2 | 3/2005 | Jeanmaire |
| 7,135,067 B2 | 11/2006 | Harz et al. |
| 7,219,989 B2 | 5/2007 | Uerz et al. |
| 7,221,440 B2 | 5/2007 | McCann et al. |
| 8,173,215 B2 | 5/2012 | Sowinski et al. |
| 8,430,492 B2 | 4/2013 | Falkner et al. |
| 8,585,189 B1 | 11/2013 | Marcus et al. |
| 8,651,632 B2 | 2/2014 | Marcus et al. |
| 8,696,094 B2 | 4/2014 | Marcus et al. |
| 8,764,161 B2 | 7/2014 | Cook et al. |
| 8,888,256 B2 | 11/2014 | Marcus et al. |
| 9,010,909 B2 | 4/2015 | Nelson et al. |
| 9,067,448 B2 | 6/2015 | Dannhauser et al. |
| 9,783,553 B1 | 10/2017 | Shukla et al. |
| 9,828,513 B2 | 11/2017 | Lussier et al. |
| 9,969,178 B1 | 5/2018 | Roberts et al. |
| 10,569,587 B1 | 2/2020 | Sowinski et al. |
| 2005/0015066 A1 | 1/2005 | Anderson et al. |
| 2006/0055750 A1 | 3/2006 | Taguchi et al. |
| 2008/0207811 A1 | 8/2008 | Brust et al. |
| 2011/0183124 A1 | 7/2011 | Aoki et al. |
| 2011/0234726 A1 | 9/2011 | Mukai et al. |
| 2016/0326390 A1* | 11/2016 | Farrugia ............... C09D 11/322 |
| 2017/0022370 A1* | 1/2017 | Farrugia ............... C09D 11/322 |
| 2018/0051184 A1 | 2/2018 | Lussier et al. |
| 2020/0129348 A1 | 4/2020 | Maldonado et al. |
| 2020/0131387 A1 | 4/2020 | Sowinski et al. |

OTHER PUBLICATIONS

International Search Report and Written Opinion; Application Ser. No. PCT/US2019/057994; dated Oct. 26, 2018, 8 pages.

U.S. Appl. No. 16/171,433, filed Oct. 26, 2018, Clarissa Maldonado et al.

International Search Report, PCT/US2019/057992, dated Feb. 14, 2020, 11 pages.

* cited by examiner

ABSORBENT ARTICLE WITH GRAPHICS PRINTED IN PRESERVATIVE-FREE INK, AND METHODS OF MANUFACTURE THEREOF

CROSS REFERENCE TO RELATED APPLICATIONS

This application is a continuation-in-part of application Ser. No. 16/171,433, filed Oct. 26, 2018, the substance of which is incorporated herein by reference.

REFERENCED APPLICATIONS

Reference is made to the following co-pending patent applications, the disclosures of all of which are incorporated herein by reference:

U.S. Ser. No. 16/171,432, filed on even date herewith by Sowinski, Bugner and Cook, and entitled "Inkjet Ink and Ink Sets";

U.S. Ser. No. 16/171,446, filed on even date herewith by Cook and Sowinski, and entitled "Fluid Sets for Inkjet Printing Methods"; and U.S. Ser. No. 16/171,455, filed on even date herewith by Sowinski, Cook, and Bugner, and entitled "Methods of Inkjet Printing".

FIELD OF THE INVENTION

The present application relates to absorbent articles bearing printed graphics, for example, feminine hygiene pads, disposable diapers, disposable training pants and adult incontinence pants and pads, designed to be worn next to the body. More particularly, the present invention relates to such products in which water-based ink(s) used to print such graphics are formulated to be free of traditional preservatives that may be deemed undesirable for use in connection with personal hygiene products.

BACKGROUND OF THE INVENTION

Disposable absorbent articles, such as feminine hygiene pads, disposable diapers, disposable training pants, and adult incontinence pads and pants, often include visual features such as printed elements on one or more surfaces for decorative or functional purposes. Decorative and/or functional printed images, designs, symbols, alphanumeric words or information ("graphics") may be printed onto surfaces of one or more material layers forming such products, to enhance consumer appeal and/or usage experience. For manufacturing processes that require relatively high-speed throughput, the preferred printing methods often include inkjet or continuous inkjet (CIJ) printing processes.

Inks used to print such graphics via inkjet or CIJ processes may be water-based or organic solvent-based. Organic solvent-based inks often contain and emit volatile organic compounds (VOCs) during and/or after printing. To reduce VOC emissions and meet increasingly stringent regulations, VOC handling and abatement systems may be needed when using such inks. These systems may require substantial capital investment and may not entirely eliminate the issue.

Alternatively, water-based inks may be used. Typical water-based ink formulations, however, may support growth of, and thereby be prone to contamination by, microbes (water-borne bacteria, yeasts and/or molds) if countermeasures are not taken. Accordingly, commercially available formulations typically include preservatives that effectively inhibit microbe growth during the time the ink is stored and awaiting use for printing.

Many of such preservatives, however, are becoming increasingly disfavored by some regulatory bodies and/or advocacy groups for use in connection with consumer personal products. Additionally, the consumer market is becoming increasingly aware of the presence of traditional preservatives in cosmetics and personal products and is developing a preference for products which do not include them.

Accordingly, there is currently an unmet need for water-based ink formulations, suitable for inkjet or CIJ printing processes, that are substantially free of traditional preservatives, while having features that preserve and/or enhance shelf life by inhibiting microbe growth and provide or maintain other balances required for suitable stability and use with inkjet printing equipment.

DETAILED DESCRIPTION

Figure 1:
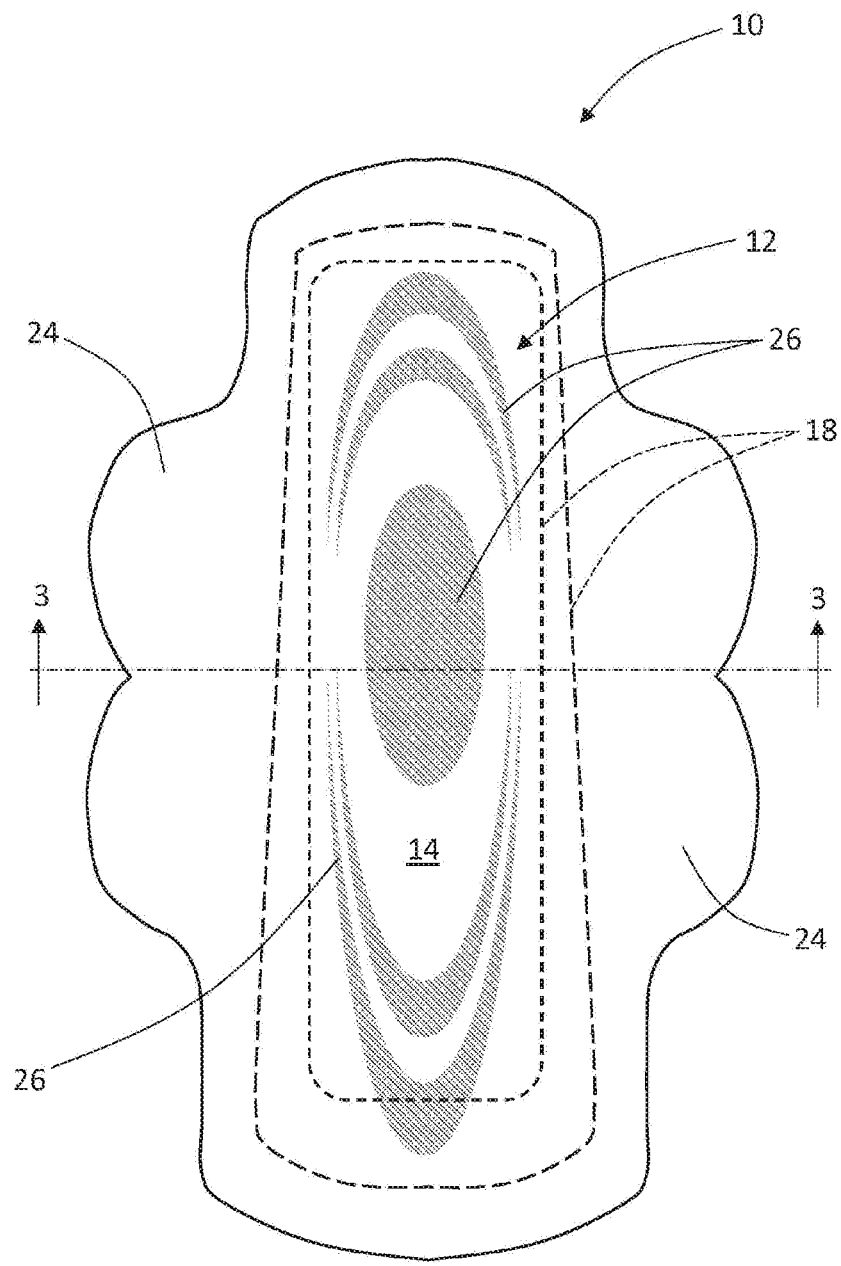
FIG. 1 is a plan view of an example of an absorbent article in the form of a feminine hygiene pad, wearer-facing surfaces facing the viewer.

The following discussion is directed to various exemplary embodiments within contemplation of the present disclosure, and while some embodiments may be desirable for specific uses, the disclosed embodiments should not be interpreted or otherwise considered to limit the scope of the claims herein. Persons of ordinary skill in the art will understand that the following disclosure has broader application than is explicitly described in the discussion of any embodiment.

The present disclosure contemplates use of inks which are substantially free of traditional preservatives to print graphics onto one or more of the component material layers of absorbent articles such as feminine hygiene pads, disposable diapers and training pants, disposable adult incontinence pants and pads, and the like.

Definitions

As used herein to define various components of the aqueous organic pigment dispersions, aqueous inkjet ink compositions, and other materials referred to herein, unless otherwise indicated, the singular forms "a", "an", and "the" are intended to include one or more of the components (that is, including plurality referents).

Each term that is not explicitly defined herein is to be understood to have a meaning that is commonly accepted by those skilled in the art. If the construction of a term would render it meaningless or essentially meaningless in its context, the term should be interpreted to have a standard dictionary meaning.

The use of numerical values in the various ranges specified herein, unless otherwise expressly indicated otherwise, are considered to be approximations as though the minimum and maximum values within the stated ranges were both preceded by the word "about". In this manner, slight variations above and below the stated ranges may be useful to achieve substantially the same results as the values within the ranges. In addition, the disclosure of these ranges is intended as a continuous range including every value between the minimum and maximum values as well as the end points of the ranges.

A "nonwoven," "nonwoven web" or "nonwoven web material" is a fabric web formed of natural fibers, spun synthetic polymeric fibers or filaments, or a combination thereof, wherein the fibers or filaments are neither woven nor knitted together, but rather, are consolidated and held together into a coherent web by a pattern of bonds, by an adhesive or binder, by mechanical entanglement, or a combination thereof.

As used herein, the parameter "acid number" (also known as acid value) is defined as the milligrams (mg) of potassium hydroxide required to neutralize 1 g of an acidic polymer.

The term "aqueous" in aqueous organic pigment dispersions, and aqueous inkjet ink compositions, according to the present disclosure means that the water content is greater than 60 weight % based on the total amount of solvents. Thus, water is the predominant solvent in the aqueous medium.

Ink and fluid dynamic viscosity may be measured by any of well-known techniques. Preferred methods include measurement of the timing of mass flow through a capillary as in a capillary viscometer, or measurement of ball drop velocity through a fluid, using for example a rolling ball viscometer. Both a capillary flow viscometer and a commercially available Anton Paar Automated MicroViscometer (AMVn) employing the rolling ball technique may be used to measure the dynamic viscosities reported herein. All ink dynamic viscosity values disclosed herein were measured under gravity induced shear at approximately 24° C. to 26° C. It will be appreciated that the values cited are reported as centipoise (cP) or milliPascal seconds (mPa-sec) and that 1 cP=$10^{-3}$ Pascal-seconds (Pa-s)=$10^{-2}$ dyne-s/cm$^2$. While viscosities may be measured with high precision, viscosity values here are reported to one or two decimal places only, and they are normally rounded values and not truncated values. All claims reciting ink viscosities are intended to be interpreted in terms of values in mPa-sec normally rounded to one decimal point. Thus, the various aqueous inkjet ink compositions may have a viscosity of up to and including 10 centipoise (10 mPa-sec).

The Wilhelmy plate method is a well-known technique for measuring the static surface tension of a liquid ink or service fluid at a solid interface. The technique involves a plate of known dimensions, typically selected from a roughened platinum alloy, suspended from a balance. The plate is contacted with a solution of interest and a vertical force is applied to the plate to form a liquid meniscus between the solution and plate. The resulting surface tension is given according to equation (1):

$$\sigma = F/L \cos(\theta) \quad (1)$$

where σ is the surface tension of the liquid, F is the force acting on the balance (milli-Newtons/meter), L is the wetted length of the plate in millimeters, and θ is the contact angle between the plate and solution.

Typically, the roughened platinum results in a contact angle very close to zero and the cosine of θ goes to 1. A complete theoretical treatment of the method may be found in, for example, "A Method for Determining Surface and Interfacial Tension Using a Wilhelmy Plate", Colloid and Polymer Science, 255 (7), pages 675-681. A number of commercially available instruments are known for measuring surface tension, however, the instrument used to report surface tension values set forth in the present disclosure is a Krüss Model K10ST tensiometer.

Pigment colorants used in the various embodiments in accordance with the present disclosure generally might not be self-dispersing, meaning that they require the presence of one or more organic polymeric pigment dispersants bound to some fraction of the surface of the pigment particles to keep them suspended in an aqueous medium.

The terms "water-soluble" and "aqueous-soluble" mean that 1 mass part of solute material may be dissolved in as little as less than 1 mass part (i.e., more soluble solute) and in as much as 1,000 mass parts (that is, less soluble solute) of distilled water at 25° C. to provide a homogeneous and visibly clear solution.

The term "solvo-surfactant" refers to a compound or combination of compounds that are effective solvents for dried "ink", and are volatile solvents having a boiling point at sea level of less than 200° C. and capable of reducing fluid surface tension and self-aggregating. Further details of such compounds are provided below.

For clarification of definitions for any terms relating to polymers, reference should be made to "Glossary of Basic Terms in Polymer Science" as published by the International Union of Pure and Applied Chemistry ("IUPAC"), Pure Appl. Chem. 68, 2287-2311 (1996). However, any definitions explicitly set forth herein should be regarded as controlling. Polymers may be prepared from ethylenically unsaturated polymerizable monomers using free radical polymerization or acid catalyzed polymerization processes, or by reaction of appropriate condensation monomers (for example diols and diisocyanates) using known condensation polymerization processes.

Unless otherwise indicated, the terms "polymer" and "polymeric" refer to both homopolymers and copolymers, each having a stated weight distribution average molecular weight ($M_w$) or a number distribution average molecular weight ($M_n$) as measured using gel permeation chromatography (polystyrene standard).

The term "copolymer" refers to polymers that are derived from two or more different monomers, in random order or a predetermined order (for example, block) along the polymer backbone. That is, each copolymer comprises at least two recurring units having different chemical structures.

The term "backbone" refers to the chain of atoms in a polymer to which a plurality of pendant groups may be attached. An example of such a backbone is an "all carbon" backbone obtained from the polymerization of one or more ethylenically unsaturated polymerizable monomers. However, other backbones may include heteroatoms wherein the polymer is formed by a condensation reaction or some other means.

Absorbent Articles

Figure 2:
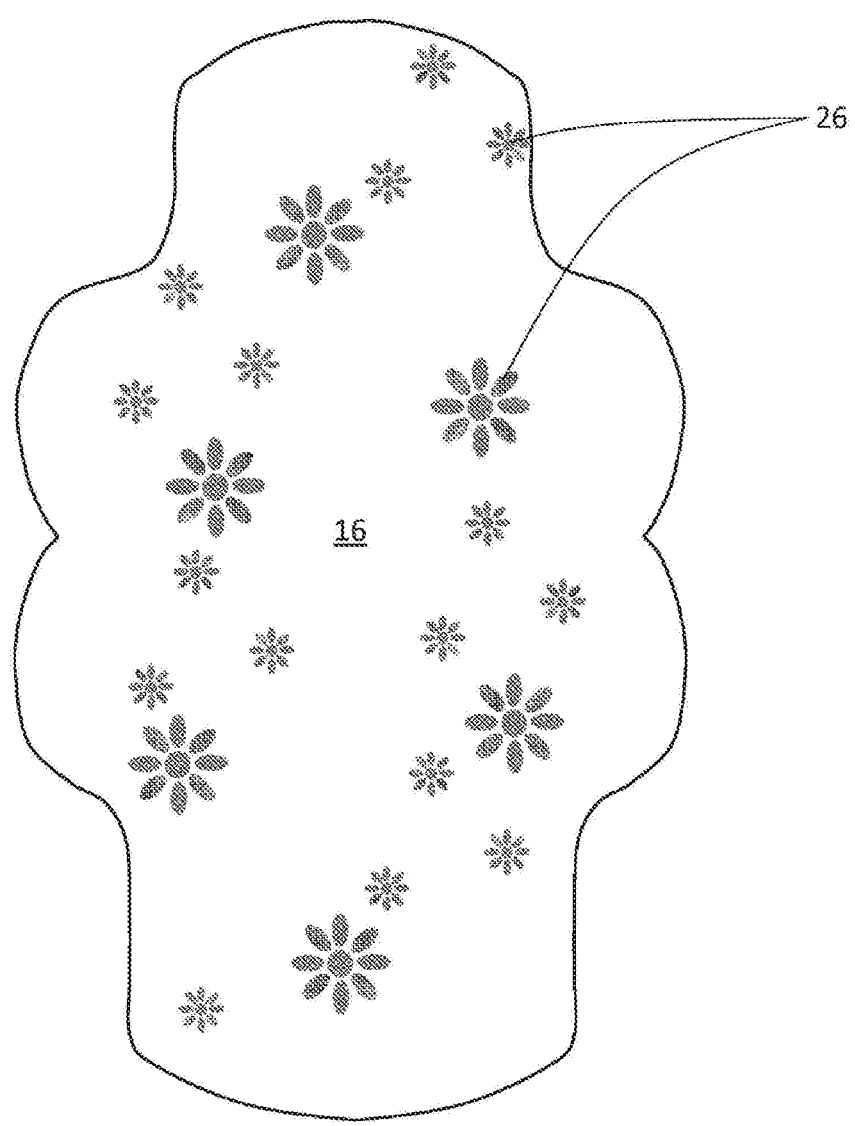
FIG. 2 is a plan view of an example of an absorbent article in the form of a feminine hygiene pad, outward-facing surfaces facing the viewer.
Figure 3:
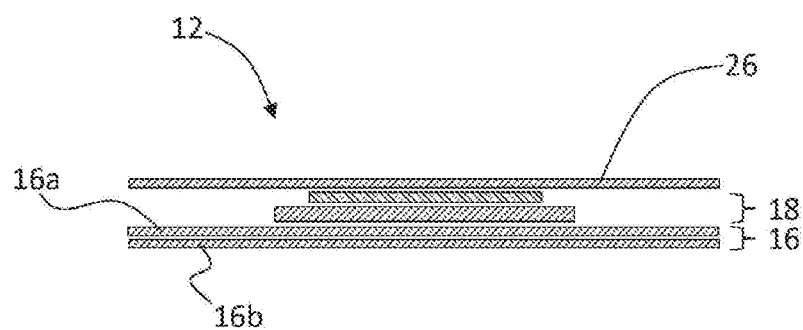
FIG. 3 is a schematic, exploded lateral cross section of components of the absorbent article shown in FIG. 1, taken along line 3-3 shown in FIG. 1.

FIGS. 1-3 depict an example of an absorbent article 10 in the form of a feminine hygiene pad, which may include a topsheet 14, a liquid impervious backsheet 16 joined to the topsheet 14, and an absorbent core structure 18 enveloped therebetween. The absorbent article, and each of its component layers, has a wearer-facing surface facing the wearer during wear, and an outward-facing surface facing away from the wearer during wear. Typically the topsheet 14 is the component layer closest the wearer during wear, and the backsheet 16 is the component layer farthest from the wearer during wear.

Absorbent article 10 may include one or more printed graphic elements 26. Graphic elements 26 may be printed on the body facing surface or the garment facing surface of the topsheet 14 so that they are readily visible. Additional graphic elements 26 may be printed on any layer of the absorbent article 10, and on either or both of the wearer-facing surface or outward-facing surface of any layer. Additional graphic elements 26 may be printed on the body facing side of the backsheet 16, on the body facing side of a secondary topsheet (not shown), on a body facing side of an absorbent core structure 18, or on a portion of a body facing side of the absorbent core structure 18. In some examples, graphic elements 26 may be printed on topsheet 14, on either the wearer-facing surface or outward-facing surface thereof. For topsheet component materials that are relatively translucent or transparent, it may be desired to print graphic elements on the outward-facing (i.e., internal) surface thereof such that the ink will be protected from frictional contact and wear, and potential resulting degradation of the visual quality of the graphic elements. Similarly, for backsheet materials that are relatively translucent or transparent, it may be desired to print graphic elements on the wearer-facing (i.e., internal) surface(s) thereof such that the ink will be protected from frictional contact and wear, and potential resulting degradation of the visual quality of the graphic elements.

The graphic elements may embody any desired combination of images, designs, ornamentation, symbols, alphanumeric characters or visible information content, and may have any desired combination of pattern, arrangement, size(s), alignment and location/placement on the article or layer component thereof. The graphic elements may be printed any single color or any combination of differing colors or individual elements of differing colors.

The graphic elements may cover any proportion of the total surface area of the printed surface, from 0% to 100%. The graphic elements may include printing in a background color of any proportion of the total surface area, with defined graphic elements printed to impart a foreground visual impression.

The absorbent article may also be provided with additional features often appearing in currently marketed feminine hygiene pads, including features sometimes identified as "wings", a secondary topsheet, a fluid acquisition layer, and/or other layers designed to be a component of and/or promote fluid transport and distribution throughout absorbent core structure 18. Likewise, topsheet 14 of the sanitary napkin may have various optional characteristics known in the art. For example, topsheet 14 may have one or more channels formed therein to direct fluid flow, apertures therethrough to facilitate fluid movement therethrough, and graphic elements 26 in the form of printed signals visible on or therethrough, the visible signals being printed on the topsheet or underlying layers for functional and esthetic effects.

The topsheet 14 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials may be included of natural fibers (e.g., wood pulp, cotton or other plant fibers (cellulose)), synthetic fibers (e.g., polymeric fibers such as polyester, polypropylene, or polyethylene fibers) or from a combination of natural and synthetic fibers. In some examples, the topsheet may be made of a hydrophobic fibrous materials, or treated to impart hydrophilicity, to promote movement of fluid through the topsheet. If the topsheet is made of a hydrophobic material, at least one, e.g., a wearer-facing or outward-facing surface of the topsheet may be treated to impart hydrophilicity so that fluids will transfer through the topsheet more rapidly. This diminishes the likelihood that body exudates will flow off the topsheet rather than being drawn through the topsheet and being absorbed by the absorbent core structure. In some examples, the topsheet may be rendered hydrophilic by applying a surfactant to it. Suitable methods for treating the topsheet with a surfactant include spraying the topsheet material with a solution containing the surfactant or immersing the material into the surfactant solution.

The topsheet may be formed of or include an apertured formed film. Apertured formed films may sometimes be desired for forming topsheets because they are pervious to body exudates and yet non-absorbent, and have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in U.S. Pat. Nos. 3,929,135; 4,324,246; 4,342,314; 4,463,045; and 5,006,394.

The absorbent core structure 18 may include any absorbent member which is generally compressible, conformable, non-irritating to the wearer's skin, and capable of absorbing and retaining body fluids. The absorbent core structure may be manufactured in a wide variety of sizes and shapes (e.g., rectangular, hourglass, "T"-shaped, asymmetric, etc.) and from a wide variety of liquid-absorbent materials commonly used in disposable pull-on garments and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; tissue including tissue wraps and tissue laminates; absorbent foams (for example, high internal phase emulsion (HIPE) foams); absorbent sponges; superabsorbent polymers; absorbent gelling materials; or any equivalent material or combinations of materials.

The configuration and construction of the absorbent core structure 18 may vary (e.g., the absorbent core structure may have varying caliper zones, a hydrophilic gradient, a superabsorbent gradient, or lower average density and lower average basis weight acquisition zones; or may include one or more layers or structures). Further, the size and absorbent capacity of the absorbent core structure may also be varied to accommodate wearers ranging from infants through adults. However, the total absorbent capacity of the absorbent core structure should be compatible with the design loading and the intended use of the absorbent article.

The absorbent core structure may include other optional components. One such optional component is the core wrap, i.e., a material, typically but not always a nonwoven material, which either partially or totally surrounds the core. Suitable core wrap materials include, but are not limited to, cellulose, hydrophilically modified nonwoven materials, perforated films and combinations thereof.

The backsheet 16 may comprise a liquid impermeable film. The backsheet may be impermeable to liquids (e.g., body fluids) under ordinary and/or balanced pressure thereacross, and may be manufactured from a thin polymeric film. In some examples the backsheet may formed so as to be vapor permeable so as to allow water vapor to escape from within the article during wear, promoting wearer comfort and skin health. In some examples, a microporous polyethylene film may be used to form the backsheet. A suitable microporous polyethylene film is manufactured by Mitsui Toatsu Chemicals, Inc., Nagoya, Japan and marketed in the trade as PG-P.

Another suitable material for the backsheet may be a liquid impervious thermoplastic film having a thickness of from about 0.012 mm (0.50 mil) to about 0.051 mm (2.0 mils), for example including polyethylene or polypropylene. The backsheet may be manufactured to have a basis weight of from about 5 g/m2 to about 35 g/m2. Additionally, other flexible liquid impervious materials may be used to form the backsheet. Herein, "flexible" refers to materials which are compliant and which will readily conform to the general shape and contours of the wearer's body.

In some examples, the backsheet 16 may be formed of a laminate of a film layer 16a of liquid-impermeable polymeric film and a backsheet nonwoven layer 16b. As noted, the polymeric film may be manufactured so as to be vapor permeable. The film layer may be desired to impart liquid impermeability, while the nonwoven layer may be desired to impart a soft, cloth-like appearance and/or tactile feel to the backsheet.

The backsheet may be positioned adjacent the outer-facing surface of the absorbent core structure and may be joined thereto, or to the topsheet by any suitable attachment device known in the art. For example, the backsheet may be secured to the absorbent core structure or to the topsheet about the perimeter of the absorbent core structure, by a uniform continuous layer of adhesive, a patterned layer of adhesive, or an array of separate lines, spirals, or spots of adhesive. Illustrative, but nonlimiting adhesives, include adhesives manufactured by H. B. Fuller Company of St. Paul, Minn., U.S.A., and marketed as HL-1358J. An example of a suitable attachment device including an open pattern network of filaments of adhesive is disclosed in U.S. Pat. No. 4,573,986. Another suitable attachment device including several lines of adhesive filaments swirled into a spiral pattern is illustrated by the apparatus and methods shown in U.S. Pat. Nos. 3,911,173; 4,785,996; and 4,842,666. Alternatively, the attachment device may include heat (thermal) bonds, pressure bonds, ultrasonic bonds, dynamic mechanical bonds, or any other suitable attachment device or combinations of these attachment devices.

The graphic elements 26 may be printed onto one or both surfaces of any component layer using one or more ink compositions comprising an aqueous organic pigment dispersion, described below.

It is common practice to provide feminine hygiene products such as feminine hygiene pads and tampons individually wrapped within wrappers, for purposes of enabling the user to conveniently carry singles or small supplies of the products with her, for example, in a handbag. The wrappers help protect the products from contamination by dirt or moisture during such carry and any handling prior to use. Such a wrapper may be formed, in some examples, of a polymeric film, a nonwoven web of spun fibers spun from polymeric resin, or a laminate of such film and a nonwoven web. It is additionally contemplated herein that graphic elements may be printed onto any surfaces of such wrappers (or layers thereof) using one or more ink compositions comprising an aqueous organic pigment dispersion, described below. Accordingly, the term "absorbent article product" used herein is deemed to include any such wrapper.

Aqueous Organic Pigment Dispersions

The one or more ink compositions each may comprise a pigment dispersion consisting of pigment colorant particles in association with a polymeric dispersant or a polymeric binder.

(a) Polymer dispersed pigment colorants within contemplation of the present disclosure may be used singly, or in combinations of two or more different polymer-dispersed pigment colorants, to provide any desired color or hue. For example, a polymer-dispersed carbon black pigment may be combined with a different polymer-dispersed colored organic pigment in the same aqueous pigment dispersion or aqueous inkjet ink composition. The exact choice of polymer-dispersed pigment colorants will depend upon the specific application, performance, color reproduction, and image stability that are desired. Examples of useful polymer-dispersed pigment colorants are described in U.S. Pat. Nos. 5,026,427; 5,141,556; 5,160,370; and 5,169,436, the disclosures of all of which are incorporated herein by reference.

Useful pigment colorants that may be dispersed with organic polymers include but are not limited to, azo pigments, monoazo pigments, disazo pigments, azo pigment lakes, β-naphthol pigments, naphthol AS pigments, benzimidazolone pigments, disazo condensation pigments, metal complex pigments, isoindolinone and isoindoline pigments, quinacridone pigments, polycyclic pigments, phthalocyanine pigments, perylene and perinone pigments, thioindigo pigments, anthrapyrimidone pigments, flavanthrone pigments, anthanthrone pigments, dioxazine pigments, triarylcarbonium pigments, quinophthalone pigments, diketopyrrolo pyrrole pigments, titanium dioxide, iron oxide, and carbon blacks. Representative useful yellow, black, green, brown, red, magenta, cyan, blue, orange, and violet pigment colorants are described in Col. 7 (line 48) to Col. 8 (line 5) of U.S. Pat. No. 8,173,215, the disclosure of which is incorporated herein by reference.

Useful pigment colorants may be accompanied or dispersed using suitable polymer dispersants that are well known in the art (as cited above). Representative useful organic polymer dispersants may be prepared from at least one anionic hydrophilic monomer such as an acrylic acid or methacrylic acid monomer, or combinations thereof, and for example, at least one monomer comprised of a hydrophobic methacrylate or acrylate monomer having an aliphatic chain having 12 or more carbon atoms, as described for example in US 2007/0043144, the disclosure of which is incorporated herein by reference. Further details of useful organic polymer dispersants, including useful monomer recurring units, monomer amounts, and $M_w$, are provided in Col. 5 (line 45) to Col. 6 (line 31) of U.S. Pat. No. 8,173,215 (noted above).

Many useful organic polymer dispersants are anionic acrylic polymers formed from at least one anionic hydrophilic monomer described above having a weight average ($M_w$) molecular weight of at least 500 Daltons but less than 100,000 Daltons, and more likely up to and including 15,000 Daltons, or up to and including 10,000 Daltons.

One or more organic polymer dispersants for the pigment colorants may be present in an amount that would be readily apparent to one skilled in the art depending upon the aqueous medium, the chosen organic pigments, and other components of the aqueous inkjet ink composition.

In addition to the polymeric dispersants, nonionic or anionic surfactants may be present with the pigment colorants as is known in the art. Representative materials of this type include but are not limited to, sodium dodecylsulfate or sodium oleylmethyltaurate as described for example in Col. 7 (lines 15-23) of U.S. Pat. No. 8,173,215 (noted above).

Particle sizes for each useful polymer-dispersed pigment colorants are as follows.

Particle size for the various polymer-dispersed pigment colorants refers to the approximate diameter of a generally spherical pigment particle or to the approximate largest characteristic dimension of a non-spherical particle. More particularly, the diameter of a sphere having the same volume as the particle is determined in practice (that is, equivalent sphere diameter). The desired median particle diameter (or 50th percentile particle diameter) of each of the pigmented colorants in accordance with the present disclosure may be less than 300 nm, less than 150 nm, less than 70 nm, or even less than 60 nm, such that 50% of the volume of the particles is composed of particles having diameters smaller than the indicated diameter. In addition, at least 95% of the total primary particles of each polymer-dispersed pigment colorant in accordance with the present disclosure have a particle diameter of less than 500 nm, less than 300 nm, less than 150 nm, or even less than 110 nm. This refers to the 95th percentile particle diameter that is the classified particle size distribution such that 95% of the volume of organic pigment particles is provided by particles having diameters smaller than the indicated diameter. Particle size (or particle volume) may be readily measured using a conventional dynamic laser light scattering particle size analyzer. Instrumental techniques for analyzing and reporting nanoparticle sizes are usefully described in "Particle Size Characterization", published by the National Institute of Standards and Technology ("NIST"), Special Publication 960-1, 93-139 (2001).

The (b) composition within contemplation of the present disclosure may consist of or include one or more compounds represented by the following Structure (I):

$$HO-CH_2-CH_2-R \quad (I)$$

wherein R is a substituted or unsubstituted phenyl group or a substituted or unsubstituted phenoxy group. For example, R may be either an unsubstituted phenyl group or an unsubstituted phenoxy group. Mixtures of compounds represented by Structure (I) may also be used.

Thus, either or both of 2-phenoxyethanol and 2-phenylethanol may be used to advantage in accordance with the present disclosure for the advantages described above. 2-Phenoxyethanol is also known as ethylene glycol phenyl ether; ethylene glycol monophenyl ether; and 1-hydroxy-2-phenoxyethane, and may be obtained as DOWANOL PhE, DOWANOL EPh, or DOWANOL EP from various commercial sources. 2-Phenylethanol is also known as phenylethanol; 2-phenylethan-1-ol; phenethyl alcohol; β-hydroxyethylbenzene; phenylethyl alcohol; β-phenylethanol; and benzyl carbinol, and may be obtained from various commercial sources.

An aqueous medium such as water and any water-miscible organic solvents, may be present in any desirable amount that would provide desired viscosity and other physical properties for storage or use of an aqueous pigment dispersion to make aqueous inkjet ink compositions.

An aqueous pigment dispersion in accordance with the present disclosure may be prepared by any method commonly used in the art, and typically involves two steps: (a) a dispersing or milling step to break up aggregates of one or more pigment colorants into primary particles wherein a primary particle is defined as the smallest identifiable subdivision in a particulate system; and (b) a dilution step in which the pigment colorant dispersion from step (a) is diluted by addition of aqueous medium and any other additives. Milling details are described for example in Col. 6 (line 58) to Col. 7 (23) of U.S. Pat. No. 8,173,215 (noted above).

Aqueous Inkjet Ink Compositions

The aqueous inkjet ink compositions in accordance with the present disclosure generally may have a dynamic viscosity that is generally less than or equal to 5 centipoise (5 mPa-sec), or at least 1 centipoise (1 mPa-sec) and up to and including 3 centipoise (3 mPa-sec), all measured at 25° C. using a rolling ball viscometer, or a capillary viscometer, and known procedures.

The aqueous inkjet ink compositions also typically may have a pH of at least 7.5 and up to and including 11, or more likely of at least 8 and up to and including 9. When the aqueous inkjet ink composition is used in hardware with nickel or nickel-plated apparatus components, a corrosion inhibitor such as the sodium salt of 2- or 5-methyl-1-H-benzotriazole may be added, and the pH may be adjusted to at least 10 and up to and including 11. If printheads fashioned out of silicon are used for inkjet printing, the aqueous inkjet ink composition pH may be adjusted to at least 7.5 and up to and including 10, or at least 8 and up to and including 9.5.

Aqueous inkjet ink compositions in accordance with the present disclosure may comprise one or more (a) polymer-dispersed pigment colorants in a total amount of at least 0.9 weight % and up to and including 6 weight %, or at least 1.5 weight % and up to and including 5 weight %, based on the total weight of the aqueous inkjet ink composition. Useful polymer-dispersed pigment colorants, and useful particle size parameters, are described above. Two or more polymer-dispersed pigment colorants may be used if desired to provide a desired hue or color in the resulting inkjet-printed image.

The (b) composition described above consisting of one or more compounds represented by Structure (I) is present in the aqueous inkjet ink compositions, in a total amount of at least 0.5 weight % and up to and including 2 weight %, or even at least 1 weight % and up to and including 1.8 weight %, based on the total weight of the aqueous inkjet ink composition.

Aqueous inkjet ink compositions contemplated by the present disclosure may comprise (c) one or more compounds selected from water-soluble humectants, co-solvents, and both water-soluble humectants and co-solvents. The co-solvents generally may be water-soluble or water-miscible organic solvents having a viscosity that is greater than 1 centipoise (1 mPa-sec) and may exceed even 40 centipoise (40 mPa-sec) when measured at 25° C. using a standard rolling ball, capillary, or spinning plate viscometer. Any water-soluble humectant or co-solvent known in the inkjet art that is compatible with the other requirements identified herein may be used. While an individual humectant may be employed, mixtures of two or more humectants, each of which imparts a useful property, may be used. Representative humectants are described for example, in U.S. Pat. No. 9,828,513, the disclosure of which is incorporated herein by reference, and include classes of compounds such as (1) mono-alcohols; (2) polyhydric alcohols; (3) lower mono- and di-alkyl ethers derived from a polyhydric alcohol; (4) nitrogen-containing compounds such as urea, 2-pyrrolidone, N-methyl-2-pyrrolidone, and 1,3-dimethyl-2-imidazolidinone; and (5) sulfur-containing compounds such as 2,2'- thiodiethanol, dimethyl sulfoxide, and tetramethylene sulfone. Useful co-solvents are also included within such classes of compounds.

The one or more (c) humectants, co-solvents, or both humectants and co-solvents may be present in an amount of less than 20 weight %, or at least 0.5 weight %, or at least 1 weight % and up to and including 15 weight %, or at least 3 weight % and up to and including 10 weight %, all based on the total weight of the aqueous inkjet ink composition. Highly preferred levels of the one or more (c) humectants, co-solvents, or both humectants and co-solvents are at least 4 weight % and up to 8 weight %.

One or more (d) supplemental antimicrobial agents may also be present in the aqueous inkjet ink compositions, and such materials are different from the (b) composition described above and represented by Structure (I). Representative materials include but are not limited to, iodopropynyl butyl carbamate (CAS 55406-53-6), piroctone olamine (CAS 68890-66-4), 2,4-dichlorobenzyl alcohol (CAS 1777-82-8), boric acid (CAS 10043-35-3) and monovalent and divalent metal ion salts derived from boric acid, and combinations of these materials. A useful amount of the one or more supplemental antimicrobial agents is at least 0.01 weight % and up to and including 3 weight %, based on the total weight of the aqueous inkjet ink composition.

Aqueous inkjet ink compositions contemplated by the present disclosure may further comprise one or more anionic polyurethanes, each having an acid number of at least 50, or of at least 60 and up to and including 150, or even at least 55 and up to and including 90, which acidic polymers are described in more detail below.

Alternatively, or in addition to the anionic polyurethanes, the aqueous inkjet ink composition may comprise one or more anionic non-aromatic acrylic or anionic styrene-acrylic polymers, each having an acid number of at least 50, or of at least 120 and up to and including 240, or even at least 160 and up to and including 220, which acidic polymers are described in more detail below. Mixtures of two or more of such materials may be used if desired.

Representative examples of both types of anionic polymers are described for example in U.S. Pat. No. 8,430,492 the disclosure of which is incorporated herein by reference, and in U.S. Pat. No. 9,783,553 (noted above). Particularly useful anionic polyurethanes contain a polyether diol unit and may be identified as polyether polyurethanes. Such anionic polyether polyurethanes generally may have a molecular weight ($M_w$) of at least 10,000 Daltons and up to and including 30,000 Daltons or at least 15,000 Daltons and up to and including 25,000 Daltons. For example, particularly useful polyether polyurethanes are individually represented by Structure (I) in U.S. Pat. No. 9,783,553 (noted above).

Useful water-soluble or water-dispersible anionic polyether polyurethanes may be prepared as described for example in [0045]-[0049] of US 2008/0207811, the disclosure of which is incorporated herein by reference. The acidic groups in the anionic polyether polyurethanes may be at least partially and up to 100% neutralized (converted into salts) using monovalent inorganic bases such as alkaline metal hydroxides or organic amines such as dimethylethanolamine.

Examples of anionic non-aromatic acrylic polymers and anionic styrene-acrylic polymers that may be useful as contemplated for purposes of the present disclosure are also described in ¶[0061] of US 2008/207811 (noted above). Examples of useful anionic styrene-acrylic polymers may include those commercially available under the trademarks JONCRYL (BASF Corp.), TRUDOT (formerly available from Mead Westvaco Co.), and VANCRYL (Allnex USA, Inc.).

The useful amounts of such anionic polymers may be up to and including 15 weight %, or up to and including 10 weight %, based on the total weight of the aqueous inkjet ink composition. Particularly useful amounts of anionic polymers range are at least 1 weight % and up to and including 5 weight %, including anionic non-aromatic acrylic polymers and anionic styrene-acrylic polymers used as the pigment dispersant.

In addition, modified polysiloxanes may be present in the aqueous inkjet inks compositions. Examples of such materials include ethoxylated or propoxylated silicone-based "surfactants" that may be obtained commercially under the trademarks SILWET (CL Witco), and BYK (Byk Chemie) such as BYK 348 and 381, as well as Dow Corning DC67, DC57, DC28, DC500W, and DC51. Non-silicone surfactants may also be used, including but not limited to anionic, cationic, nonionic, or amphoteric surfactants such as those commercially available as SURFYNOL surfactants (Evonik Corp.) including SURFYNOL 440 and 465 alkynediol surfactants. Useful amounts of such materials are readily apparent to one skilled in the art. Particularly useful amounts of selected surfactants are described in U.S. Pat. No. 8,455,570, the disclosure of which is herein incorporated by reference.

It may be useful to include one or more "promoters" in the aqueous inkjet ink compositions potentially to enhance the effectiveness of the compounds represented by Structure (I) in the (b) composition. Such materials are generally alkane diols, each having at least 7 carbon atoms and up to and including 12 carbon atoms, and particularly having at least 7 carbon atoms and up to and including 10 carbon atoms. Representative useful compounds that may be used singly or in combination as promoters include but are not limited to, 1,7-heptanediol, 1,2-heptandiol, 2-ethyl-1,3-hexanediol, 1,2-octandiol, 3,6-octanediol, 2,2,4-trimethyl-1,3-pentandiol, 1,2-nonanediol, 1,10-decanediol, 1,12-dodecanediol, and others that would be readily apparent to one skilled in the art. 1,2-Octanediol is particularly useful in this regard.

One or more promoters may be present in the aqueous inkjet ink compositions at a total amount of less than or equal to 1.5 weight % or less than or equal to 1.25 weight %, based on the total weight of the aqueous inkjet ink composition. A minimum amount may be at least 0.3 weight %.

Colorless fluorescent colorants (dyes or pigments) may also be present in the aqueous inkjet ink compositions in amounts readily apparent to one skilled in the art, and examples of such compounds are described in US 2014/231674, the disclosure of which is incorporated herein by reference.

Other additives that may be present in the aqueous inkjet ink compositions, in amounts that would be readily apparent to one skilled in the art, include but are not limited to: surfactants besides those described above to adjust composition surface tension, including but not limited to the TERGITOL 15-S and TMN series nonionic surfactants, BRIJ series nonionic surfactants; TRITON series nonionic surfactants, ZONYL fluoro surfactants; PLURONIC nonionic surfactants; TETRONIC nonionic surfactants, SILWET nonionic surfactants, and SURFYNOL nonionic surfactants, and various anionic and cationic surfactants mentioned in Col. 10, line 64 to Col. 11, line 14 of U.S. Pat. No. 8,173,215 (noted above)]; thickeners; conductivity-enhancing agents; drying agents; waterfast agents; viscosity modifiers; pH buffers; antifoamants; wetting agents; corrosion inhibitors; antifoamants and defoamers (such as SURFYNOL DF-110L, PC, MD-20, and DF-70); UV radiation absorbers; antioxidants; and light stabilizers available under the trademarks TINUVIN (BASF Corp.) and IRGANOX (BASF Corp.), as well as other additives described in Col. 17 (lines 11-36) of U.S. Pat. No. 8,455,570 (noted above). The useful amounts of such materials would be readily apparent to one skilled in the art using routine experimentation.

Water is generally present in each aqueous inkjet ink as the primary aqueous medium, in a suitable amount such as at least 75 weight % or at least 80 weight %, and generally at no more than 90 weight %, based on the total weight of the aqueous inkjet ink composition.

Each aqueous inkjet ink composition described herein may be prepared by dispersing suitable polymer-dispersed pigments colorants in water, and mixing in other noted materials such as the (b) compounds represented by Structure (I), (c) humectants or co-solvents, and any adjuvants, promoters, supplemental antimicrobial agents, and additional materials in suitable amounts.

Ink Sets

Ink sets are contemplated by the present disclosure, and they may include two or more aqueous inkjet ink compositions, each of which comprises at least one visible polymer-dispersed pigment colorant (described above) to provide a desired color or hue. For example, an ink set may include useful aqueous inkjet ink compositions which may have different hues or "colors" such as various shades of orange, red, violet, green, cyan, yellow, black, magenta, brown, pink, and blue and thus contain one or more suitable polymer-dispersed pigment colorants suitable to provide the desired hue. Any desirable hue, for example as defined using known a* and b* CIELAB values, may be provided by proper use and formulation of suitable polymer-dispersed pigment colorants. Aqueous "white" inkjet ink compositions also may be useful in certain situations and may be included in an ink set. A wide variety of organic and inorganic pigments may be used individually or in combination in such aqueous inkjet ink compositions, as described above, and they may have the desired pigment particle size as described above. The polymer-dispersed pigment colorants may be present in suitable amounts as described above for the aqueous inkjet ink compositions in accordance with the present disclosure.

In addition to the polymer-dispersed pigment colorants, one or more of the aqueous color inkjet ink compositions in an ink set may include one or more aqueous-soluble dyes that are well known in the art, for example as described in Col. 12 (lines 4-55) of U.S. Pat. No. 8,455,570 (noted above).

The aqueous inkjet ink compositions in the ink sets may be formulated the same as or differently from those described above.

Each aqueous color inkjet ink compositions in an ink set may have a desirable pH of at least 7.5 and up to and including 11, or at least 8 and up to and including 10, as described above using suitable bases and buffer systems.

In addition, each aqueous color inkjet ink composition may have suitable dynamic viscosity of at least 1 centipoise (1 mPa-sec) but less than 5 centipoise (5 mPa-sec) as measured at 25° C.

Each of the aqueous inkjet ink compositions in an ink set independently comprises (has same or different): (a) a polymer-dispersed pigment colorant (as described above) in an amount of at least 0.9 weight % and up to and including 6 weight %, based on the total weight of the aqueous inkjet ink composition; a (b) composition consisting of compounds represented by Structure (I) as described above; and (c) at least one water-soluble humectant, co-solvent, or a combination of water-soluble humectant and co-solvent, all as described above and in the amounts described above.

For example, an ink set according to the present disclosure may have two or more of the following specific types of aqueous inkjet ink compositions:

(i) an aqueous inkjet ink composition comprising a polymer-dispersed cyan pigment colorant, (ii) an aqueous inkjet ink composition comprising a polymer-dispersed magenta pigment colorant, (iii) an aqueous inkjet ink composition comprising a polymer-dispersed yellow pigment colorant, and (iv) an aqueous inkjet ink composition comprising a polymer-dispersed black pigment colorant.

In many ink sets, all four (i) through (iv) aqueous inkjet ink compositions may be present.

In some embodiments, an ink set according to the present disclosure may further comprise a particle-free colorless inkjet composition (or aqueous particle-free fluid), for example as described in U.S. Pat. No. 8,764,161 (noted above), the disclosure of which is incorporated herein by reference. Such compositions may be known as "fluids" in the art and may have various purposes or functions such as printhead maintenance, storage, flushing, or cleaning, or use as replenishment fluids. The details of such fluids are provided in the cited patent, the disclosure of which is incorporated herein by reference. By "particle-free", it is meant that such compositions do not purposely contain particulates or pigments of any type, colorless or colored. Further details of useful such fluids are provided below in the discussion of individual aqueous particle-free "fluid sets".

Such particle-free colorless inkjet compositions may also comprise a (b) composition consisting of compounds represented by Structure (I) described above, which compounds may be the same as or different from those used in the two or more aqueous inkjet ink compositions in an ink set containing a polymer-dispersed pigment colorant. For example, such particle-free colorless inkjet compositions may contain 2-phenoxyethanol, 2-phenylethanol, or both 2-phenoxyethanol and 2-phenylethanol [as when R is 2-phenyl or 2-phenoxy in Structure (I)] in an amount of at least 0.5 weight % and up to and including 2 weight %, based on the total weight of the particle-free colorless inkjet composition.

The durability, gloss, and other properties of an inkjet printed image may be improved by the application of a colorless polymeric overcoat composition, which may be considered an aqueous particle-free inkjet composition in accordance with the present disclosure. Examples of such compositions are provided in U.S. Pat. No. 7,219,989. In other to achieve high inkjet printing speeds and throughput associated with CIJ printing, such an overcoat composition may be applied using a CIJ printhead following in-line with one or more printheads of drop-forming nozzles dispensing "colored" aqueous inkjet ink compositions. Further details about such application are provided in Col. 17 (lines 16-48) of U.S. Pat. No. 8,173,215 (noted above).

Additional aqueous particle-free inkjet compositions (or inks) that may be part of an ink set include those described in US 2018/0051184 that may be inkjet printed to provide colorless or colored coatings, the disclosure of which publication is incorporated herein by reference. Such compositions may comprise at the least, one or more anionic polyether polyurethanes or anionic acrylic or styrene-acrylic polymers as described above, as well as a suitable antifoamant or defoamer to reducing foaming propensities. Such aqueous particle-free inkjet compositions may further comprise a (b) composition having compounds defined by Structure (I) as described above.

Each component or composition present in an ink set, whether colored or colorless, may contain various other additives (such as defoamers, surfactants, conductivity enhancing agents, drying agents, water-fast agents, chelating agents, thickeners, anti-kogation agents, stabilizers, and buffering agents) that would be readily apparent to one skilled in the art.

Aqueous Particle-Free Fluids

Aqueous particle-free fluids may be designed and used for various purposes contemplated by the present disclosure. Each of these aqueous particle-free fluids generally independently has a dynamic viscosity of less than or equal to 5 centipoise (5 mPa-sec) at 25° C. for example as measured using a rolling ball viscometer, or a capillary viscometer, and standard procedures. Each of these aqueous particle-free fluids purposely contains no particles, colorless or otherwise, and may be used for various purposes or functions in inkjet printing methods, as described below.

Two or more of such aqueous particle-free fluids, having the same or different purposes, may be incorporated into a "fluid set" for commercialization if desired. Alternatively, one or more of the aqueous particle-free fluids may be included within the ink sets described above.

Each aqueous particle-free fluid independently may have a pH broadly similar to the aqueous inkjet ink compositions described above, that is, of at least 5 and up to and including 11. pH may be managed for each aqueous particle-free fluid using the teaching in Col. 11 (line 58) to Col. 12 (line 26) of U.S. Pat. No. 8,764,161 (noted above). In some embodiments, the pH is at least 10 and up to and including 11, and may be managed by the presence of one or more bases, as described below.

An aqueous particle-free fluid according to the present disclosure may independently consist essentially of a (b) composition consisting of one or more compounds represented by Structure (I) as defined above. Individual aqueous particle-free fluids in a fluid set may have the same or different (b) composition. The one or more compounds in the (b) composition, for example those wherein R is 2-phenyl or 2-phenoxy, may be present in an aqueous particle-free fluid in an amount of at least 0.5 weight % and up to and including 2 weight %, based on the total weight of the aqueous particle-free fluid.

In a particular embodiment, the aqueous particle-free fluids may have different general compositions aside from their (b) composition and are suitable for two or more different printing service functions. For example, a "replenisher" aqueous particle-free fluid may be used to restore evaporated solvent from the aqueous inkjet ink composition in the ink tank and return that composition to a previous colorant concentration. Such aqueous particle-free fluids generally consist essentially of only the (b) composition described above. However, it is possible for such aqueous particle-free fluids to additionally include a humectant, co-solvent, supplemental antimicrobial agent, surfactant, promoter, or any combination thereof, as described in more detail below. For example, such aqueous particle-free fluids may desirably also contain any volatile organic solvents that are lost to evaporation during ink recycling, or a weak organic base (for example, an alkanolamine) to mitigate pH drift due to carbonic acid formation resulting from carbon dioxide uptake. Since a continuous inkjet printer fluid system method of determining the relative concentration of the ink in the ink tank is to measure the ink's ionic conductivity (or alternatively its resistivity), it is undesirable to alter the restored ink fluid properties and ion inventory materially with contributions that accumulate from repeated replenisher addition. Thus, it is desired to minimize the replenisher aqueous particle-free fluid content of for example, organic solvents, humectants, pH and ionic conductivity modifying additives, polymer compounds, surfactants, and antifoamants.

A "maintenance" aqueous particle-free fluid, a printhead cleaner and storage fluid, may be used to re-dissolve, re-disperse, or solubilize dried ink deposits that form on and around the nozzleplate nozzles and interfere with inkjet straightness and inkjet stability. It may then be used to purge the printhead ink channels and external surfaces to flush ink away. The aqueous particle-free fluid is also suitable for keeping the wetted parts ready for efficient start-ups after periods of extended storage, but the various printhead and fluid system maintenance functions of flushing, cleaning, and storage may be accomplished by specialized individual aqueous particle-free fluids as desired.

In addition to a (b) composition, a printhead cleaner and storage aqueous particle-free fluid according to the present disclosure may desirably include an organic solvent that improves upon the effectiveness of the fluid vehicle (water) in penetrating and solvating dried pigment particles in deposits of dried aqueous inkjet ink composition. It may additionally contain optional additives that include but are not limited to a solubilizing agent, a co-solvent, viscosity modifiers, a base, an acid, a pH buffer, a chelating agent, a dispersant, a water-soluble or water-dispersible polymer, a corrosion inhibitor, a viscosity modifier, a penetrant, a wetting agent, an antifoamant, and a defoamer. Effective solvents for dried aqueous inkjet ink composition may be selected from the class of dynamic surface tension reducing co-solvents also known in the art as penetrants, where the dynamic surface tension reducing polar co-solvent agent is also considered a functional surface tension modifying agent (that is, it is aptly referred to as a "solvo-surfactant" that is a low molecular weight, volatile solvent with an amphiphilic composition capable of reducing fluid surface tension and capable of self-aggregating). On a molar and mass fraction basis, such solvo-solvents are less effective surface modifying agents than the traditional surfactants for reducing equilibrium surface tension. Solvo-surfactants employed for removal of dried aqueous inkjet ink composition desirably comprise an asymmetric polyhydric alcohol or mono-alkyl ether derived from a polyhydric alcohol. Specific examples of lower ($C_1$-$C_4$) mono-alkyl ethers and derivatives originating from polyhydric alcohols include but are not limited to ethylene glycol monomethyl ether, ethylene glycol monobutyl ether, ethylene glycol monoethyl ether acetate, diethylene glycol monomethyl ether, diethylene glycol monobutyl ether, triethylene glycol monobutyl ether, polyethylene glycol monobutyl ether, propylene glycol monomethyl ether, propylene glycol monopropyl ether and diethylene glycol monobutyl ether acetate, among others all as supplied as the DOWANOL, CELLUSOLVE and CARBITOL series of compounds by Dow Chemical Co. Such solvo-surfactants, alone or in combination, may be used at amounts of at least 0.1 weight % and up to and including 20 weight %, or even in an amount of at least 3 weight % and up to and including 6 weight %, all based on the total weight of the aqueous particle-free fluid.

Increased fluid pH may be beneficial to the removal of dried aqueous inkjet ink composition, and printhead cleaner aqueous particle-free pH is optionally raised with organic bases, such as aliphatic amines substituted with hydroxyl groups (for example, alkanolamines), including monoethanolamine, diethanolamine, 3-amino-1-propanol, N-methylethanolamine, N-benzyl-N-methylethanolamine, 2-(2-aminoethoxy)ethanol, N,N-dimethyl-2-(2-aminoethoxy)ethanol, N-methyldiethanolamine, N,N-dimethylethanolamine, and triethanolamine. High pH aqueous particle-free fluids may have a pH of at least 10 and up to and including 11.

The wetting of contaminated printhead parts is critical to successful cleaning. If sufficient solvo-surfactant is employed, no additional dynamic or static surface tension modifier may be needed. Otherwise, a surfactant may be included. Representative compounds of these types are described in Col. 12 (lines 27-62) of U.S. Pat. No. 8,764,161 (noted above), the disclosure of which is incorporated herein by reference. One or more surfactants that may be anionic, cationic, amphoteric or nonionic in nature may be present in the aqueous particle-free fluid in an amount of at least 0.01 weight % and up to and including 10 weight %, based on the total weight of the aqueous particle-free fluid. While any agent that serves to control the surface tension at large surface ages may be usefully employed, the surfactant desirably has a weight-normalized molecular weight below about 1,000 Daltons. While the charged surfactants may have slower diffusion in aqueous fluids due to the aggregated water of hydration which effectively increases their bound mass, the useful non-ionic surfactants desirably have a molecular weight above 350 Daltons, above 400 Daltons, or even above 500 Daltons, to ensure slow diffusion in bulk ink so as to allow distinct control of static or equilibrium surface tensions. Examples of suitable nonionic surfactants include but are not limited to, linear or secondary alcohol ethoxylates (such as the TERGITOL 15-S and TERGITOL TMN series of compounds available from Dow Chemical Company and the BRIJ series of compounds from Croda International Plc.), ethoxylated alkyl phenols (such as the TRITON series of compounds from Dow Chemical Company), fluoro surfactants (such as the ZONYL compounds from DuPont; and the FLUORAD compounds from 3M), fatty acid ethoxylates, fatty amide ethoxylates, ethoxylated and propoxylated block copolymers (such as the PLURONIC and TETRONIC series of compounds from BASF Corp., ethoxylated and propoxylated silicone based surfactants (such as the SILWET series of compounds from Momentive), alkyl polyglycosides (such as the GLUCOPON compounds from BASF Corp.) and acetylenic diol polyethylene oxide surfactants (such as the SURFYNOL family of compounds from Evonik Corp.). The polymeric surfactants may be water soluble or water dispersible depending in part on their tendency to aggregate. A useful surfactant blend suitable for dispersing pigments and re-dispersing dried aqueous inkjet ink compound is ZETASPERSE 1600 (Evonik Corp.).

In addition, styrene-acrylic type polymers may be used in the printhead cleaner and storage fluid. The water-soluble or water-dispersible polymeric components may be the same or similar to the polymers described above for use as polymeric dispersants for pigment colorants, or the anionic polymers incorporated into aqueous inkjet ink compositions. Such materials are present in the aqueous inkjet ink compositions to improve physical durability of an inkjet printed image, or to improve other characteristics of the compositions such as colloidal stability to gear pump mediated recirculating filtration. For example, such water-soluble or water-dispersible polymeric components may be random or block copolymers having both hydrophilic and hydrophobic recurring units derived from the corresponding ethylenically unsaturated polymerizable monomers. They may be "acrylics" and "styrene-acrylics" that are derived primarily from styrene monomers, and (meth)acrylic acid, or (meth)acrylate ester monomers. Some useful water-soluble or water-dispersible polymeric components may be derived from the various monomers and teaching provided in Col. 7 (line 24) to Col. 8 (line 55) of U.S. Pat. No. 8,764,161 (noted above). Other useful (3) water-soluble or water-dispersible polymeric compounds may be water-soluble polymers having poly(ethylene-oxide) segments and water-dispersible polyurethanes, for example, as described in Col. 10 (lines 24-46) of U.S. Pat. No. 8,764,161 (noted above). Mixtures of two or more of the same or different classes of these materials may be used if desired.

One or more water-soluble or water-dispersible polymeric components may be present in each aqueous particle-free fluid independently in an amount of up to and including 20 weight %, or at least 0.2 weight % and up to and including 10 weight %, or even at least 0.5 weight % and up to and including 8 weight %, or more likely in an amount of at least 2 weight % and up to and including 5 weight %, all based on the total weight of the aqueous particle-free fluid.

The aqueous particle-free fluids used for printhead cleaning and storage service desirably contain a humectant, co-solvent, or both, to facilitate inkjet printing start-up after an extended period of time without printing. Any water-soluble humectant or co-solvent known in the inkjet art and compatible with the other requirements described herein may be employed. By water-soluble is meant that a mixture of the employed humectant(s) or co-solvent(s) and water are adequately homogeneous and not subject to spontaneous phase separation. While an individual humectant or co-solvent may be employed, useful aqueous particle-free fluid compositions may employ mixtures of two, three, or more humectants and co-solvents, each of which imparts a useful property. Representative examples of humectants and co-solvents used in aqueous-based ink compositions include (1) alcohols, such as methyl alcohol, ethyl alcohol, n-propyl alcohol, isopropyl alcohol, n-butyl alcohol, sec-butyl alcohol, t-butyl alcohol, iso-butyl alcohol, furfuryl alcohol, and tetrahydrofurfuryl alcohol; (2) polyhydric alcohols, such as ethylene glycol, di(ethylene glycol), tri(ethylene glycol), tetra(ethylene glycol), propylene glycol, di(propylene glycol), the poly(ethylene glycol)s with average molecular weights ranging from 200 to about 5000 Daltons (particularly poly(ethylene glycol)-400 (average $M_n$ of about 400, herein referred to as PEG-400 for convenience)), the polypropylene glycols with average molecular weights ranging from 200 to about 5000 Daltons (particularly poly(propylene glycol)-425 (average $M_n$ of about 425)), 1,2-propanediol, 1,3-propanediol, 1,2-butanediol, 1,3-butanediol, 1,4-butanediol, 1,2,4-butanetriol, 3-methyl-1,3-butanediol, 2-methyl-1,3-propanediol, 1,5-pentanediol, 1,6-hexanediol, 2-methyl-2,4-pentanediol, 1,7-heptanediol, 2-ethyl-1,3-hexanediol, 2,2,4-trimethyl-1,3-pentanediol, 1,8-octanediol, glycerol, 1,2,6-hexanetriol, 2-ethyl-2-hydroxymethyl-propanediol, 2-methyl-2-hydroxymethyl-propanediol, saccharides and sugar alcohols and thioglycol; (3) polyoxygenated polyols and their derivatives such as diglycerol, polyglycerols, glycerol ethoxides, glycerol propoxides, glyceryths, alkylated and acetylated glyceryths, saccharide such as sorbitol or fructose, pentaerythritol, pentaerythritol ethoxides, and pentaerythritol propoxides and their alkylated and acetylated derivatives. Particularly desirable ingredients serving primarily as a humectant to retard aqueous particle-free fluid drying and aid aqueous inkjet ink composition redispersability include glycerol, ethylene glycol, diethylene glycol, triethylene glycol, related polyols, and the polyhydric alcohol derivatives thereof, which are desirable. Triethylene glycol is particularly useful. The total humectant and co-solvent level of the fluid or ink is the sum of the individual contributions of humectant or miscible polar organic co-solvent, DST-modifying co-solvent (solvo-surfactant), and any other co-solvent ingredients, which may include humectant or organic co-solvent added directly or incidentally during the totality of aqueous particle-free fluid or ink formulation (for example, co-solvent associated with a commercial biocide preparation as a supplemental ingredient, or with a commercial pigment dispersion preparation that may be present to prevent so-called "paint-flakes" of dried pigment cake forming around a bottle cap, as described in U.S. Publication No. 2005/0075415 (Harz et al). The one or more (c) humectants, co-solvents, or both humectants and co-solvents may be present in the aqueous particle-free fluid in an amount of less than 20 weight %, or of at least 0.5 weight %, or at least 1 weight % and up to and including 15 weight %, or at least 3 weight % and up to and including 10 weight %, all based on the total weight of the aqueous particle-free fluid. More desirably, the total humectant and co-solvent level is less than or equal to 10 weight %.

Each aqueous particle-free fluid may further contain one or more promoters for the one or more compounds in the (b) composition potentially to enhance the effectiveness of the compounds represented by Structure (I). As described above, such promoters are generally alkane diols, each having at least 7 carbon atoms and up to and including 12 carbon atoms, and particularly having at least 7 carbon atoms and up to and including 10 carbon atoms. Representative useful compounds that may be used singly or in combination as promoters are described above. 1,2-Octanediol is particularly useful as a promoter in this regard.

One or more promoters may be present in each aqueous particle-free fluid at a total amount of less than or equal to 1.5 weight % or less than or equal to 1.25 weight %, based on the total weight of the aqueous inkjet ink composition. A minimum amount may be at least 0.3 weight %.

One or more (d) supplemental antimicrobial compounds may also be present independently in each aqueous particle-free fluid in a fluid set, and such materials are different from the (b) composition described above. Representative materials include but are not limited to, iodopropynyl butyl carbamate (CAS 55406-53-6), piroctone olamine (CAS 68890-66-4), 2,4-dichlorobenzyl alcohol (CAS 1777-82-8), boric acid (CAS 10043-35-3) and monovalent and divalent metal ion salts derived from boric acid, and combinations of any of these materials. A useful amount of the one or more supplemental antimicrobial agents is at least 0.01 weight % and up to and including 3 weight %, based on the total weight of the aqueous particle-free fluid.

Methods of Inkjet Printing

Details regarding the various methods and apparatus useful for inkjet printing are provided in numerous publications, but as best understood none of that art describes such methods being carried out using the (b) composition having compounds represented by Structure (I) defined above, or the advantages achieved according to the present invention.

Methods according to the present disclosure may be carried out by, firstly, providing a suitable substrate for printing. Any individual substrate will have what would be understood as having at least one surface with a "printable" area onto which an aqueous inkjet ink composition may be ink jetted using suitable equipment and processes.

Suitable substrates are typically planar in nature with two opposing surfaces or supporting sides, one or both of which may be inkjet-printed to provide the same or different images. Substrates may have a single "layer" or stratum or be composed of multiple layers or strata composed of the same or different materials. In some examples, a substrate has a predominant material, such as a cellulosic material that is coated or layered with one or more other types of materials such as polymeric coatings.

Inkjet printable substrates can include the various polymeric films, nonwoven fabrics and absorbent foams used to form components of absorbent articles as described herein. A substrate may be transparent, translucent, or opaque, and it may be provided for inkjet printing in the form of a rigid or semi-rigid sheet, cut or continuous film or web, or wound roll.

Durability and other properties of inkjet-printed color images may be improved by using substrates that have been pretreated with a composition to enhance the quality of the resulting images. This pretreatment is typically done prior to incorporation of the substrate into the inkjet printing apparatus (such as a continuous inkjet printing apparatus), but in some instances, the substrate may be pretreated within the apparatus before inkjet printing with one or more aqueous inkjet ink compositions. One or both opposing surfaces (planar sides) of a substrate may be pretreated, or one supporting surface may be pretreated and the opposite supporting surface left untreated.

For example, a substrate may be pretreated with a pretreatment composition comprising a water-soluble multivalent metal ion salt, such as but not limited to, a salt comprising one or more multivalent cations including calcium, magnesium, barium, zinc, and aluminum cations, with calcium and magnesium cations being particularly useful. Examples of useful multivalent metal cation salts to provide such cations are known in the art as useful salts may be determined by a skilled artisan. Details of such pretreatment procedures and compositions are provided for example, in U.S. Pat. No. 9,067,448, the disclosure of which is incorporated herein by reference.

An aqueous inkjet ink composition according to the present disclosure [as described above having the required viscosity and all (a) polymer-dispersed pigment colorant(s), (b) composition consisting of Structure (I) compounds, and (c) compounds] may be inkjet-printed from a suitable printhead in a controlled manner onto at least one surface of the substrate to provide an inkjet-printed image on that surface of the substrate.

While aqueous inkjet ink compositions according to the present disclosure may be useful in one or more DOD printing systems, the advantages may be particularly evident when CIJ printing processes and equipment are used. There are several CIJ printing processes known in the art, and the present disclosure does not contemplate limitation to any particular CIJ process. There may be certain CIJ processes, however, that may be more useful than others for purposes of the present disclosure. In general, such CIJ processes may use one or more aqueous inkjet ink compositions that are ejected through one or more printheads (containing nozzles), and unprinted aqueous inkjet ink composition is collected and recycled through the printing system multiple times until it is used up. In addition, the CIJ printing system may have incorporated replenisher systems. Details of such CIJ processes and equipment are provided for example in U.S. Pat. No. 8,173,215 (noted above).

Thus, in most CIJ inkjet printing processes, each aqueous inkjet ink composition according to the present disclosure may be ejected or printed from a main fluid supply dedicated to it only, as a continuous stream of the aqueous inkjet ink composition that is broken into both printing drops and non-printing drops. The non-printing drops of each aqueous inkjet ink composition may be collected using suitable collecting means such as a "catcher" and returned to its respective main fluid supply. This entire scenario may be carried out using a single (first) aqueous inkjet ink composition alone, or in combination with one or more "additional" aqueous inkjet ink compositions having the same or different "colors" or hues as the first aqueous inkjet ink composition. The multiple aqueous inkjet ink compositions are then inkjet printed in a chosen sequence that may be controlled by particular software and digital input, in a controlled manner, to provide a multicolor inkjet printed-image on the surface of the substrate.

In addition, inkjet printing of an aqueous "colorless" or aqueous particle-free composition or fluid (as described above) may be carried out simultaneously or sequentially with inkjet printing of the "colored" aqueous inkjet ink composition(s). For example, according to US 2018/0051184, a colorless lacquer or protective coating may be applied over single- or multicolor inkjet-printed images.

As is implied herein, each aqueous inkjet ink composition, aqueous colorless composition, or aqueous particle-free composition of fluid used in such processes may be designed according to the present disclosure to comprise the described (a) one or more polymer-dispersed pigment colorants (only for the aqueous inkjet ink compositions), described (b) composition consisting of compounds defined by Structure (I), and described (c) compounds. However, any such aqueous compositions used in the method according to the present disclosure may further include one or more (d) supplemental antimicrobial compounds that are all different from the (b) composition.

Useful CIJ printing processes and equipment may include replenishment systems that measure ink electrical resistivity and are described for example in U.S. Pat. No. 5,526,026, the disclosure of which is incorporated herein by reference and in EP 0597628B1. Useful CIJ printing processes and equipment that employ other means for ink concentration sensing are disclosed in U.S. Pat. No. 7,221,440, the disclosure of which is incorporated herein by reference, and in EP 0571784B1 and EP 1,013,450B1.

In one embodiment, basic replenishment is carried out as follows: a fluid system contains an ink resistivity measurement cell through which aqueous inkjet ink composition passes as it is being recirculated through the ink handling portion of the system, including the printhead. A calculation means determines the resistance of the ink resistivity cell. A logic and control unit, responsive to the calculation means, controls the transfer of aqueous inkjet ink composition from a supplemental "ink" supply and the transfer of an aqueous particle-free fluid ("carrier fluid") from a replenishment carrier fluid supply to the system main fluid supply, to maintain desired resistivity in the aqueous inkjet ink composition. The volume of the aqueous inkjet ink composition is monitored by a float valve position, and when a predetermined volume has been depleted, the predetermined volume is replaced by either aqueous inkjet ink composition from the supplemental "ink" supply or by carrier fluid from the replenishment carrier fluid supply.

Thus, the first and any additional aqueous inkjet ink compositions may be replenished, respectively, with first and any additional aqueous inkjet ink compositions, each of which consists essentially of the same or different (a), (b), and (c) components described above, and especially the same or different (b) composition that consists of compounds defined by Structure (I) noted above.

In other examples, a method according to the present disclosure may further include replenishing a main fluid supply with an aqueous particle-free fluid that has a dynamic viscosity of less than or equal to 5 centipoise (5 mPa-sec) at 25° C., which aqueous particle-free fluid may consist essentially of: the same or different (b) composition that is present in the first aqueous inkjet ink composition, as described above.

Such aqueous particle-free fluid may further comprise a (d) supplemental antimicrobial compound, as described above, that is different from the (b) composition. For example, the (d) supplemental antimicrobial compound may be iodopropynyl butyl carbamate, piroctone olamine, 2,4-dichlorobenzyl alcohol, boric acid, or a combination of these compounds.

The aqueous particle-free fluid used for replenishment may also contain one or more promoters for the one or more (b) compounds, each of which promoter is an alkane diol having a least 7 carbon atoms and up to and including 12 carbon atoms, in an amount of less than or equal to 1.5 weight %, based on the total weight of the aqueous inkjet ink composition. For example, the promoter may be 1,2-octanediol.

In some embodiments, a method according to the present disclosure may be carried out using a plurality of printing drops formed from a continuous fluid stream, and non-printing drops of a different volume than the printing drops are diverted by a drop deflection means into a "gutter" for collection and recirculation. Details about such CIJ printing systems and equipment are provided for example in U.S. Pat. Nos. 6,588,888; 6,554,410; 6,682,182; 6,793,328; 6,866,370; 6,575,566; 6,517,197; and US 2002/0202054, the disclosures of all of which are incorporated herein by reference.

In other embodiments, an aqueous inkjet ink composition may be printed using an apparatus capable of controlling the direction of the formed printing drops and non-printing drops by asymmetric application of heat to the fluid stream that initializes drop breakup and serves to steer the resultant drop as described for example in U.S. Pat. Nos. 6,079,821 and 6,505,921, the disclosure of both of which are incorporated herein by reference. Useful agitation, heated supply, printhead, and fluid filtration means for CIJ printing are described for example in U.S. Pat. No. 6,817,705, the disclosure of which is incorporated herein by reference.

A simple schematic of a CIJ printing system is provided in FIG. 1 of U.S. Pat. No. 8,764,161 (noted above).

Moreover, in some embodiments, a method according to the present disclosure may further include:

stopping the inkjet printing of the first aqueous inkjet ink composition;

delivering an aqueous particle-free fluid (as described above) from a maintenance fluid supply to the printhead; and ejecting the aqueous particle-free fluid from the printhead to purge the first aqueous inkjet ink composition from the printhead, wherein the aqueous particle-free fluid that has a dynamic viscosity of less than or equal to 5 centipoise (5 mPa-sec) at 25° C. as measured using a rolling ball viscometer and consists essentially of:

the same or different (b) composition that is present in the first aqueous inkjet ink composition, as described above.

Such aqueous particle-free fluid may further contain less than or equal to 15 weight % of one or more compounds selected from water-soluble humectants, co-solvents, and both water-soluble humectants and co-solvents, based on the total weight of the aqueous particle-free fluid.

Moreover, it may further contain one or more promoters for the (b) composition, each of which promoter is an alkane diol having a least 7 carbon atoms and up to and including 12 carbon atoms, in an amount of less than or equal to 1.5 weight %, based on the total weight of the aqueous particle-free fluid.

The aqueous particle-free fluid used in this series of steps may be considered a "maintenance fluid" that is used to clean the printheads at selected intervals or when a printing job is completed or interrupted for some reason. The maintenance fluid may be stored in a printhead for a period of time, and delivery of first or additional aqueous inkjet ink compositions from the main and any other respective fluid supplies to the respective printheads may be subsequently restarted for a new printing procedure.

Further details about use of an aqueous particle-free composition as a maintenance fluid in this manner are provided in U.S. Pat. No. 8,764,161 (noted above).

In some embodiments in according with the present disclosure, a method of printing an image using a continuous inkjet printer system, may include:

providing a substrate (as described above);

providing a jetting module having a plurality of nozzles including a nozzle in fluid communication with a main fluid supply containing a first aqueous inkjet ink composition (such equipment would be readily known to one skilled in the art in view of teaching in U.S. Pat. No. 9,010,909 the disclosure of which is incorporated herein by reference);

causing drops of the first aqueous inkjet ink composition to be formed while it is jetted through the nozzle in fluid communication with the main fluid supply by drop stimulation in response to time-varying electrical signals (equipment used to perform this function would be readily apparent to one skilled in the art in view of teaching in U.S. Pat. No. 9,010,909);

providing a catcher including a drop contact face (known to one skilled in the art in view of teaching in U.S. Pat. No. 9,010,909 (noted above));

using a deflection mechanism to deflect at least some of the drops of the first aqueous inkjet ink composition onto the drop contact face of the catcher while allowing other drops of the first aqueous inkjet ink composition to pass by the catcher and to be deposited onto a surface of the substrate (known to one skilled in the art in view of teaching in U.S. Pat. No. 9,010,909 (noted above)); and causing the drops of the aqueous inkjet ink composition that contact the drop contact face to flow along the drop contact face (known to known skilled in the art in view of teaching in U.S. Pat. No. 9,010,909 (noted above)), wherein the first aqueous inkjet ink composition has a dynamic viscosity of less than or equal to 5 centipoise (5 mPa-sec) at 25° C., and consists essentially of:

(a) one or more polymer-dispersed pigment colorants (as described above) in a total amount of at least 0.9 weight % and up to and including 6 weight %, based on the total weight of the aqueous inkjet ink composition;

(b) a composition (as described above) consisting of one or more compounds represented by the following Structure I:

$$HO-CH_2-CH_2-R \quad (I)$$

wherein R is a substituted or unsubstituted phenyl group or a substituted or unsubstituted phenoxy group, in a total amount of at least 0.5 weight % and up to and including 2 weight %, based on the total weight of the aqueous inkjet ink composition;

(c) less than or equal to 15 weight % of one or more compounds (as described above) selected from water-soluble humectants, co-solvents, and both water-soluble humectants and co-solvents, based on the total weight of the aqueous inkjet composition, wherein each of the one or more polymer-dispersed pigment colorants has a $50^{th}$ percentile particle diameter of less than 70 nm and a $95^{th}$ percentile particle diameter of less than 150 nm, all particle diameters being measured using a dynamic light scattering particle size analyzer.

In some embodiments, the least some of the drops (deflected drops) of the first aqueous inkjet ink composition used in the noted method, are smaller than the other drops (non-deflected and deposited drops) of the first aqueous inkjet ink composition.

In still other embodiments, the least some of the drops (deflected drops) of the first aqueous inkjet ink composition are larger than the other drops (non-deflected and deposited drops) of the first aqueous inkjet ink composition.

Moreover, a method in accordance with the present disclosure for continuous inkjet (CIJ) printing may include:

supplying a main fluid supply of a continuous inkjet printer (as known in the art) with a first aqueous inkjet ink composition (as described above) having a dynamic viscosity of less than or equal to 5 centipoise (5 mPa-sec) at 25° C., and consisting essentially of:

(a) one or more polymer-dispersed pigment colorants (as described above) in a total amount of at least 0.9 weight % and up to and including 6 weight %, based on the total weight of the aqueous inkjet ink composition;

(b) a composition (as described above) consisting of one or more compounds represented by the following Structure I:

$$HO-CH_2-CH_2-R \quad (I)$$

wherein R is a substituted or unsubstituted phenyl group or a substituted or unsubstituted phenoxy group, in a total amount of at least 0.5 weight % and up to and including 2 weight %, based on the total weight of the aqueous inkjet ink composition;

(c) less than or equal to 15 weight % of one or more compounds (as described above) selected from water-soluble humectants, co-solvents, and both water-soluble humectants and co-solvents, based on the total weight of the aqueous inkjet composition, wherein each of the one or more polymer-dispersed pigment colorants has a $50^{th}$ percentile particle diameter of less than 70 nm and a $95^{th}$ percentile particle diameter of less than 150 nm, all particle diameters being measured using a dynamic light scattering particle size analyzer;

ejecting a continuous stream of drops of the first aqueous inkjet ink composition from a drop generator mechanism (as known in the art);

in response to electrical signals received from a control mechanism, selecting between printing drops for imaging a substrate and nonprinting drops that are collected and returned to the main fluid supply, both types of drops from the first aqueous inkjet ink composition; and replenishing the main fluid supply as a function of resistivity of the first aqueous inkjet ink composition in the main fluid supply. Replenishment may be achieved using replenishing first aqueous inkjet ink composition, or a replenishing aqueous particle-free fluid, as described above.

Additional CIJ printing processes and details of useful CIJ apparatus are described for example in U.S. Pat. Nos. 8,585,189; 8,651,632; 8,696,094; 8,888,256; and 9,969,178, all of which disclosures are incorporated herein by reference.

Printed Articles

A resulting inkjet printed article (or printed substrate) may have a monochrome or multicolor image on at least one supporting surface of an absorbent article.

In the following preparations and examples, the pigment dispersion reported pigment content is based on the weight percent of the as-received colorant in the final dispersion. Preparation of Aqueous Inkjet Ink and Service Fluid Compositions Polymeric Dispersant and Additive Preparation:

Polymeric Dispersant P-1

In a representative procedure, a 5-liter, three-necked, round bottom flask equipped with a mechanical stirrer, a reflux condenser, and a gas inlet was charged with 225 g of 1-methoxy-2-propanol and was sparged with nitrogen. Akzo-Nobel Chemicals, Inc., initiator PERKADOX AMBN-GR (1.9 g) was added with stirring. A reactant reservoir was charged with 225 g of 1-methoxy-2-propanol, 23.4 g of 1-dodecanethiol, 203.5 g of benzyl methacrylate, 165.0 g of stearyl methacrylate, and 181.5 g of methacrylic acid, and the solution was degassed by nitrogen sparging. PERKADOX AMBN-GR (7.7 g) was added and mixed in. The reactor temperature was raised to 77° C. and the reactants were pumped from the reservoir at a about 2.3 ml/min over a 360-minute period. The reaction mixture was then stirred for at least 12 hours at about 77° C. The resulting polymer was neutralized to completion with N,N-dimethylethanolamine and stirred for 45 minutes. The reaction mixture was diluted with 2,580 g of water and filtered through a Pall Corp. ULTIPLEAT polypropylene cartridge filter. The final polymer solution of Polymeric Dispersant P-1 had a concentration of about 20 weight % solids and its pH was 8.6. The polymer weight-average molecular weight was 9,070 Daltons.

Polymeric Dispersant P-2

Polymeric dispersant P-2 was prepared in a similar fashion to P-1, except that 90% of the acid was reacted with potassium hydroxide during the neutralization step instead of with one equivalent of N,N-dimethylethanolamine. The final polymer solution of Polymeric Dispersant P-2 had a concentration of about 17 weight % solids.

Polymeric Additive P-3

A benzyl methacrylate-methacrylic acid copolymer having monomer weight ratio 77:23 and acid number of about 137 was 90%-neutralized with potassium hydroxide to provide an aqueous solution. The final polymer solution of Polymeric Additive P-3 had a concentration of about 25 weight % solids.

Polymeric Additive P-4

BASF Dispersions & Pigments North America JONCRYL HPD 696, which is a styrene acrylic copolymer having a weight-average molecular weight $M_w$ of 16,000 Daltons, was 90%-neutralized with potassium hydroxide to provide an aqueous solution. The final polymer solution of Polymeric Additive P-4 had a concentration of about 20 weight % solids.

Polymeric Additive P-5

In a 50-liter, round bottom flask equipped with thermometer, stirrer, water condenser, nitrogen inlet, and a vacuum outlet were placed 1,454.4 g of TERATHANE 2000 polyether glycol, 670.5 g of 2,2-bis(hydroxymethyl) propionic acid, 313.2 g of 1,4-butanediol, and 3,771 g of ethyl acetate. The temperature was adjusted to 65° C., and when a homogeneous solution was obtained, 1,840.9 g of isophorone diisocyanate was added, followed by 184 g of ethyl acetate. The temperature was raised to 78° C. and maintained for 22 hours to complete the reaction. The reaction mixture was then diluted with 86 g of 2-propanol before being neutralized with 467.9 g of N,N-dimethylethanolamine. Under high shear, 18 kg of distilled water was added and the organic solvents were subsequently removed by distillation under vacuum. The resultant aqueous dispersion was filtered and was determined to have a non-volatile solids concentration of about 25 weight % and a pH value of about 8.0. The weight-average molecular weight ($M_w$) of the polyurethane dispersion was found by size exclusion chromatography to be about 19,800.

Pigment Dispersion Preparations:

Pigment Dispersion KD-1

To a 2.5-gallon (9.46 liter), 9-inch (22.9 cm) diameter and 12-inch (30.5 cm) deep, double-walled stainless-steel mixing vessel containing four baffles were added water (1,000 g) and a solution of Polymeric Dispersant P-1 (1,000 g of a 19.9 weight % solution). A nominal 4-inch (10.2 cm), ring-style disperser impeller (Hockmeyer Equipment Corp. D-Blade) driven by a Charles Ross & Son Co. Model HSM-100LH-2 High Shear Mixer was centered 2 inches (5.1 cm) above the bottom of the mixing vessel, and stirring was initiated. Cabot Corp. BLACK PEARLS 900 carbon black pigment (500 g) was slowly integrated into the fluid. Milling media comprising beads of polystyrene resin (copolymer derived from styrene and a divinyl benzene/ethylvinyl benzene mixture) with an average particle diameter of 50 μm (3,000 g) was added slowly while increasing impeller speed. The mixture was milled with an impeller blade tip speed of about 19 m/sec for about 20 hours at an internal temperature of 25-35° C. Samples were periodically removed, diluted, and filtered for particle size determination by a Microtrac, Inc., NANOTRAC NPA 150 dynamic light scattering particle size analyzer. When milling was complete, the dispersion/media milling mixture was further diluted with a solution of water (1,667 g) to a final pigment concentration of about 12 weight %, a polymeric dispersant concentration of about 4.8 weight % including the counterion, and a theoretical dispersion batch size of about 4,167 g. The impeller was removed and the milling media was separated from the dispersion by filtration. A final filtration through a 0.3-μm removal efficiency Pall Corp. PROFILE II depth filter gave roughly 4 kg of dispersion, approximately 80% yield. The volume-weighted $50^{th}$ percentile particle size distribution diameter was about 55 nm, and the 95$^{th}$ percentile particle size distribution diameter was about 99 nm as characterized by the NANOTRAC NPA 150 dynamic light scattering particle sizing instrument.

Pigment Dispersion MD-1

Magenta pigment dispersion MD-1 was prepared in a similar manner to pigment dispersion KD-1, except that BASF Dispersions & Pigments North America CINQUA-SIA Magenta D 4500 J was used in place of carbon black pigment. The resulting dispersion had approximately 12 weight % pigment and 6.1 weight % polymeric dispersant, including the counterion. The volume-weighted median particle size was about 16 nm and the 95$^{th}$ percentile particle size distribution diameter was about 59 nm as characterized by the NANOTRAC NPA 150 dynamic light scattering particle sizing instrument.

Pigment Dispersion CD-1

Cyan pigment dispersion CD-1 was prepared in a similar manner to pigment dispersion KD-1, except that Pigment Blue 15:4 and Pigment Green 7 were used in a ratio of 3.75:1 in place of carbon black pigment and polymeric dispersant P-2 was used in place of P-1 in the presence of Lubrizol Corp. SOLSPERSE 12000 and Polymeric Additive P-3. The resulting dispersion had approximately 12 weight % pigment and 8.5 weight % polymer dispersant, including the counterion. The volume-weighted 50$^{th}$ percentile particle size distribution diameter is about 28 nm, and the 95$^{th}$ percentile particle size distribution diameter is about 86 nm as characterized by the NANOTRAC NPA 150 dynamic light scattering particle sizing instrument.

Pigment Dispersion YD-1

To a 10-gallon (37.85 liter), 13-inch (33 cm) diameter and 17-inch (43.2 cm) deep, double-walled stainless-steel mixing vessel containing four baffles were added 2,560 g water and 2,400 g of a 15% solution of Polymeric Dispersant P-2. A nominal 6-inch (15.2 cm) ring-style disperser impeller (Hockmeyer Equipment Corp. D-Blade) driven by a Hockmeyer Model HBI-7.5-11-99 High Shear Mixer was centered 3 inches (7.6 cm) above the bottom of the mixing vessel, and stirring was initiated. Sun Chemical Co. Pigment Yellow 74 (1,200 g) was slowly added to the fluid. Milling media comprising polymeric beads derived from styrene and a divinyl benzene/ethylvinyl benzene mixture with an average particle diameter of 50 μm (7,200 g) were added slowly while increasing impeller speed. The mixture was milled with an impeller blade tip speed of about 20 meters/second for about 20 hours at an internal temperature of 25-30° C. The dispersion/media mixture was further diluted with water (6,000 g) to a final pigment concentration of about 12 weight % and a Polymeric Additive P-2 concentration of about 4.1 weight %. The impeller was removed and the dispersion was separated from the milling media by filtration. A final filtration through a 0.3 μm particle removal rating Pall Corp. PROFILE II depth filter yielded roughly 10.6 kg of dispersion. The volume-weighted 50$^{th}$ percentile particle size distribution diameter of the dispersion was about 11 nm, and the 95$^{th}$ percentile particle size distribution diameter was about 16 nm as determined by a NANOTRAC NPA 150 dynamic light scattering particle sizing instrument.

Preparation of Continuous Inkjet Ink and Service Fluid Compositions:

Aqueous Black Inkjet Ink Composition

Black pigmented CIJ aqueous inkjet ink composition K-A (E) was prepared using pigment dispersion KD-1 by combining the components at the relative proportions reported in the following TABLE I. In a representative procedure, 15.0 kg of aqueous inkjet ink composition was mixed by adding the components individually to a 30-liter cross-linked, high density polyethylene flat bottom tank using a 2-inch (5.1 cm) impeller rotating at about 1,000 rpm to provide good mixing. The ingredients (if so indicated) were added in the following functional component order: water, acid or acid solution, amine-acid salt solution, humectant and organic co-solvent, amine base, metal corrosion inhibitor, preservative or biocide, solvo-surfactant, soluble azo dye, pigment dispersion, surfactant, and antifoamant. The aqueous inkjet ink composition was mixed for about 2 minutes between ingredient additions, and then it was stirred for 1 hour after the final addition of the surfactant or antifoamant. The aqueous inkjet ink composition was filtered through Pall Corp. 0.2 μm effective pore size ULTIPOR N66 cartridge filter media at a rate of about 0.5 liter/min/inch (0.2 liter/min/cm) of media. The pigment particles in the resulting aqueous inkjet ink composition had a volume-weighted 50$^{th}$ percentile particle size of 53 nm and 95th percentile particle size of 79 nm, a pH of about 8.6, electrical conductivity of 1.14 mS/cm, dynamic viscosity of 1.60 mPa-sec at 25° C., density of 1.035 g/cm$^3$ at 25° C., and a static surface tension of 37.2 mN/m at 25° C.

TABLE I

| Functional Component | Component | Ink K-A (E) (weight %) |
|---|---|---|
| Vehicle | Water | 48.8 |
| Pigment Dispersion | KD-1 | 33.8 |
| Binder Polymer Dispersion | P-5 | 7.2 |
| Humectant | Glycerol | 8.5 |
| Metal Corrosion Inhibitor | COBRATEC TT-50S (PMC Specialties Group, Inc.) | 0.1 |
| Solvo-surfactant | 2-Phenylethanol (Acros Organics) | 1.5 |
| Surfactant | SURFYNOL 440 (Evonik Corp.) | 0.2 |

Aqueous Cyan Inkjet Ink Compositions

Aqueous cyan CIJ inkjet ink compositions C-A through C-C were prepared from the pigment dispersion CD-1 by combining the components at the relative proportions shown below in TABLE II in a manner analogous to that described for the aqueous inkjet ink composition K-A. These inkjet ink compositions exhibited physical properties that are reported below in TABLE III.

TABLE II

| Functional Component | Ingredient | C-A (C) (weight %) | C-B (E) (weight %) | C-C (E) (weight %) |
|---|---|---|---|---|
| Vehicle | Water | 74.1 | 72.6 | 72.6 |
| Pigment Dispersion | CD-1 | 16.7 | 16.7 | 16.7 |

TABLE II-continued

| Functional Component | Ingredient | C-A (C) (weight %) | C-B (E) (weight %) | C-C (E) (weight %) |
|---|---|---|---|---|
| Binder Polymer Dispersion | P-5 | 4.0 | 4.0 | 4.0 |
| Stabilizer Polymer | LUVITEC K 17 (BASF) | 0.5 | 0.5 | 0.5 |
| Humectant | Glycerol | 4.0 | 4.0 | 4.0 |
| Metal Corrosion Inhibitor | COBRATEC TT-50S (PMC Specialties Group, Inc.) | 0.1 | 0.1 | 0.1 |
| Solvo-surfactant | 2-Phenoxyethanol (Sigma-Aldrich) | 0.0 | 1.5 | 0.0 |
| Solvo-surfactant | 2-Phenylethanol (Acros Organics) | 0.0 | 0.0 | 1.5 |
| Surfactant | SURFYNOL 440 (Evonik Corp.) | 0.1 | 0.1 | 0.1 |
| Antifoamant | SURFYNOL DF-110D (Evonik Corp.) | 0.1 | 0.1 | 0.1 |

TABLE III

| Properties | C-A (C) | C-B (E) | C-C (E) |
|---|---|---|---|
| Particle Size $50^{th}$ percentile (nm) | 28 | 29 | 30 |
| Particle Size $95^{th}$ percentile (nm) | 86 | 84 | 81 |
| pH | 8.5 | 8.4 | 8.4 |
| Conductivity (mS/cm) | 1.99 | 2.05 | 2.12 |
| Density, 25° C. (g/cm$^3$) | 1.023 | 1.024 | 1.022 |
| Dynamic Viscosity, at 25° C. in mPa-sec | 1.34 | 1.40 | 1.40 |
| Static Surface Tension, at 25° C. in mN/m | 37.8 | 36.7 | 36.5 |

Aqueous Magenta Inkjet Ink Compositions

Aqueous magenta CIJ inkjet ink compositions M-A through M-C were prepared from the pigment dispersion MD-1 by combining the components at the relative proportions reported below in TABLE IV in a manner analogous to that described for the aqueous black inkjet ink K-A. These aqueous magenta inkjet ink compositions exhibited physical properties that are reported below in TABLE V.

TABLE IV

| Functional Component | Component | M-A (C) (weight %) | M-B (E) (weight %) | M-C (E) (weight %) |
|---|---|---|---|---|
| Vehicle | Water | 55.4 | 53.9 | 53.9 |
| Pigment Dispersion | MD-1 | 31.7 | 31.7 | 31.7 |
| Binder Polymer Dispersion | P-5 | 6.0 | 6.0 | 6.0 |
| Humectant | Glycerol | 6.5 | 6.5 | 6.5 |
| Metal Corrosion Inhibitor | COBRATEC TT-50S (PMC Specialties Group, Inc.) | 0.1 | 0.1 | 0.1 |
| Solvo-surfactant | 2-Phenoxyethanol (Sigma-Aldrich) | 0.0 | 1.5 | 0.0 |
| Solvo-surfactant | 2-Phenylethanol (Acros Organics) | 0.0 | 0.0 | 1.5 |
| Surfactant | SURFYNOL 440 (Evonik Corp.) | 0.22 | 0.22 | 0.22 |
| Antifoamant | SURFYNOL DF-110D (Evonik Corp.) | 0.1 | 0.1 | 0.1 |

TABLE V

| Properties | M-A (C) | M-B (E) | M-C (E) |
|---|---|---|---|
| Particle Size $50^{th}$ percentile (nm) | 15 | 14 | 15 |
| Particle Size $95^{th}$ percentile (nm) | 60 | 59 | 57 |
| pH | 8.7 | 8.6 | 8.6 |
| Conductivity (mS/cm) | 1.51 | 1.50 | 1.52 |
| Density, 25° C. (g/cm$^3$) | 1.033 | 1.035 | 1.033 |
| Dynamic Viscosity, at 25° C. in mPa-sec | 1.74 | 1.87 | 1.83 |
| Static Surface Tension, at 25° C. in mN/m | 38.7 | 37.1 | 36.8 |

Aqueous Yellow Inkjet Ink Composition

Aqueous yellow CIJ inkjet ink composition Y-A (E) was prepared from the pigment dispersion YD-1 by combining the components at the relative proportions reported below in TABLE VI in a manner analogous to that described for the aqueous inkjet ink composition K-A.

TABLE VI

| Functional Component | Component | Y-A (E) (weight %) |
|---|---|---|
| Vehicle | Water | 60.9 |
| Pigment Dispersion | YD-1 | 25.0 |
| Binder Polymer Solution | P-4 | 4.0 |
| Binder Polymer Dispersion | P-5 | 3.3 |
| Humectant | Triethylene glycol | 5.0 |
| Metal Corrosion Inhibitor | COBRATEC TT-50S (PMC Specialties Group, Inc.) | 0.1 |
| Solvo-surfactant | 2-Phenylethanol (Acros Organics) | 1.5 |
| Surfactant | SURFYNOL 440 (Evonik Corp.) | 0.1 |
| Antifoamant | SURFYNOL DF-110D (Evonik Corp.) | 0.1 |

The pigment particles in this aqueous inkjet ink composition had a volume-weighted $50^{th}$ percentile particle size of 12 nm and a $95^{th}$ percentile particle size of 31 nm as characterized by the NANOTRAC NPA 150 dynamic light scattering particle sizing instrument. It also had a pH of about 8.4, electrical conductivity of 2.26 mS/cm, dynamic viscosity of 1.62 mPa-sec at 25° C., density of 1.020 g/cm$^3$ at 25° C., and a static surface tension of 36.3 mN/m at 25° C.

Continuous Inkjet Printing (CIJ) Replenisher Fluid

CIJ Replenisher Fluids R-A (E) and R-B (E) were prepared by combining the components shown below in TABLE VII at the relative proportions in a manner analogous to that described for aqueous black inkjet ink composition K-A. These aqueous particle-free fluids exhibited physical properties that are shown below in TABLE VIII.

TABLE VII

| Functional Component | Component | Fluid R-A (E) (weight %) | Fluid R-B (E) (weight %) |
|---|---|---|---|
| Vehicle | Water | 99.0 | 99.0 |
| Solvo-surfactant | 2-Phenoxyethanol (Dow Chemical Co.) | 1.0 | 0.0 |
| Solvo-surfactant | 2-Phenylethanol (Acros Organics) | 0.0 | 1.0 |

TABLE VIII

| Properties | Fluid R-A (E) | Fluid R-B (E) |
|---|---|---|
| pH | 6.5 | 6.2 |
| Conductivity (mS/cm) | 0.001 | 0.001 |
| Density, at 25° C. in g/cm$^3$ | 0.999 | 0.998 |
| Dynamic Viscosity, at 25° C. in mPa-sec | 1.018 | 0.923 |
| Static Surface Tension, at 25° C. in mN/m | 46.9 | 46.1 |

Continuous Inkjet Printing (CIJ) Printhead Cleaner and Storage Fluid

CIJ Printhead Cleaner and Storage Fluids S-A (C) and S-B (E) were prepared by combining the components below in TABLE IX at the relative proportions in a manner analogous to that described for the aqueous black inkjet ink composition K-A. These aqueous particle-free fluids exhibited physical properties that are shown below in TABLE X.

TABLE IX

| Functional Component | Component | Fluid S-A (C) (weight %) | Fluid S-B (E) (weight %) |
|---|---|---|---|
| Vehicle | Water | 83.7 | 81.3 |
| Base | N,N-Dimethylaminoethanol | 0.1 | 0.5 |
| Acid | Acetic acid, 25% | 0.1 | 1.2 |
| Humectant | Triethylene glycol | 10.0 | 10.0 |
| Metal Corrosion Inhibitor | COBRATEC TT-50S (PMC Specialties Group, Inc.) | 0.1 | 0.1 |
| Solvo-surfactant | Diethylene glycol monobutyl ether | 5.0 | 5.0 |
| Solvo-surfactant | 2-Phenoxyethanol (Dow Chemical Co.) | 0.0 | 1.0 |
| Surfactant | ZETASPERSEC ® 1600 (Evonik Corp.) | 1.0 | 1.0 |

TABLE X

| Properties | Fluid S-A (C) | Fluid S-B (E) |
|---|---|---|
| pH | 9.2 | 8.6 |
| Conductivity (mS/cm) | 0.44 | 2.12 |
| Density, at 25° C. in g/cm$^3$ | 1.015 | 1.017 |
| Dynamic Viscosity at 25° C. in mPa-sec | 1.64 | 1.65 |
| Static Surface Tension, at 25° C. in mN/m | 28.3 | 29.3 |

Microbiological Growth Susceptibility Testing

The aqueous inkjet ink compositions described above were subjected to a Ten Challenge preservative efficacy test employing cultured strains of particular microorganisms. The test organisms were individually cultured to known concentrations of colony forming units (CFU) and they were then mixed together and inoculated into 50 grams of the aqueous inkjet ink composition test sample. At specified time intervals, the inoculated sample was tested. The surviving population of inoculum was evaluated by streaking a Trypticase Soy Agar plate with 10 µl of well-mixed sample and incubating. The presence of microorganisms was documented using the growth ratings shown in the following TABLE XI. Each sample was re-inoculated and evaluated up to ten times over the course of the study, while any changes in the physical appearance of the sample were observed.

TABLE XI

| Growth Rating | Microorganism Colonies |
|---|---|
| 1 | 0 |
| 2 | 1 to 4 |
| 3 | 5 to 10 |
| 4 | 11 to 25 |
| 5 | 26 to 50 |
| 6 | 51 to 100 |
| 7 | 101 to 200 |
| 8 | 201 to 300 |
| 9 | TNTC* |
| 10 | Confluent growth |

*TNTC means "too numerous to count"

The following TABLE XII reports the 10 Challenge growth rating test results for the previously described aqueous inkjet ink compositions ("ink"), wherein the initial baseline growth rating for microorganisms in the as-received composition was determined to be "1". The column identified with "R—OH" denotes the absence or presence of solvo-surfactant 2-phenoxyethanol (PhE) or 2-phenylethanol (PEA) in the sample.

TABLE XII

| Entry | Ink | R-OH | 1 | 2 | 3 | 4 | 5 | 6 | 7 | 8 | 9 | 10 |
|---|---|---|---|---|---|---|---|---|---|---|---|---|
| 1 (C) | C-A | — | 9 | 9 | 6 | 9 | 6 | 9 | 9 | 9 | 9 | 6 |
| 2 (E) | C-B | PhE | 1 | 1 | 1 | 1 | 1 | 2 | 1 | 2 | 1 | 1 |
| 3 (E) | C-C | PEA | 1 | 1 | 1 | 1 | 1 | 1 | 1 | 1 | 1 | 1 |
| 4 (C) | M-A | — | 1 | 4 | 2 | 2 | 5 | 4 | 5 | 4 | 2 | 2 |
| 5 (E) | M-B | PhE | 1 | 1 | 1 | 1 | 1 | 1 | 1 | 1 | 1 | 1 |
| 6 (E) | M-C | PEA | 1 | 1 | 1 | 1 | 1 | 1 | 1 | 1 | 1 | 1 |
| 7 (E) | Y-A | PEA | 1 | 1 | 1 | 1 | 1 | 1 | 1 | 1 | 1 | 1 |
| 8 (E) | K-A | PEA | 1 | 1 | 1 | 1 | 1 | 1 | 1 | 1 | 1 | 1 |

The results shown in TABLE XII indicate that considerable microorganism growth (high colony counts) was observed in the comparative composition ("ink") C-A (C)

and M-A (C) after the first few inoculations. The data in TABLE XII also reveal that the presence of 2-phenoxyethanol (PhE) in inventive compositions ("Inks") C-B (E) and M-B (E) or 2-phenylethanol (PEA) in inventive compositions ("Inks") C-C (E), M-C (E), Y-A (E), and K-A (E) resulted in minimal or undetectable microbial growth through all ten challenges.

In an identical manner to the aqueous inkjet ink compositions, the aqueous particle-free fluids were subjected to a Ten Challenge preservative efficacy test employing the same cultured strains of particular microorganisms. The following TABLE XIII shows the 10 Challenge growth rating test results for those fluids, wherein the initial baseline growth rating for microorganisms in the as-received fluids was determined to be "1". The column identified with "R—OH" denotes the absence or presence of solvo-surfactant 2-phenoxyethanol (PhE) or 2-phenylethanol (PEA) in the fluid.

TABLE XIII

| Entry | Fluid | R-OH | 1 | 2 | 3 | 4 | 5 | 6 | 7 | 8 | 9 | 10 |
|---|---|---|---|---|---|---|---|---|---|---|---|---|
| 1 (E) | R-A | PhE | 1 | 2 | 4 | 7 | 5 | 2 | 1 | 2 | 2 | 4 |
| 2 (E) | R-B | PEA | 2 | 1 | 1 | 1 | 1 | 6 | 6 | 6 | 4 | 6 |
| 3 (C) | S-A | — | 1 | 1 | 1 | 1 | 1 | 1 | 3 | 1 | 1 | 1 |
| 4 (E) | S-B | PhE | 1 | 1 | 1 | 1 | 1 | 1 | 1 | 1 | 1 | 1 |

The results reported in TABLE XIII show that significant microorganism growth (increased colony counts) was observed in the inventive Replenisher Fluids R-A (E) and R-B (E) after the first few inoculations, but the result is expected to be better than a replenisher fluid comprised purely of water without any solvo-surfactant. The results in TABLE XIII also show that virtually no microorganism growth was observed in the comparative Printhead Cleaning and Storage Fluid S-A (C), which contained solvo-surfactant diethylene glycol monobutyl ether as a dried ink cleaning agent; only challenge No. 7 produced a significant growth rating of 3. However, the presence of 2-phenoxyethanol (PhE) in inventive Printhead Cleaning and Storage Fluid S-B (E) produced undetectable microbial growth through all ten challenges.

It will be appreciated that embodiments of ink and fluid formulations described above may be suitably resistant to growth of contaminating microorganisms without containing any substantial amounts of, that is, being substantially free of, commonly used preservatives such as isothiazolinone compounds and formaldehyde releasing compounds (like 2-bromo-2-nitropropane-1,3-diol; hexamethylenetetramine chloroallyl chloride) and biocides currently listed in the List of Approved Active Substances (Article 95 List) published by the European Chemical Agency (ECHA) (an agency of the European Union).

Continuous Inkjet Printing of Aqueous Inkjet Ink Compositions

In a representative procedure, the ink reservoir of a continuous inkjet printing test stand fixture was charged with inventive aqueous cyan inkjet ink composition C-C (E). Repetitive cycles of draining, flushing, and filling the ink reservoir and fluid lines with C-C (E) were carried out to ensure that the new composition was not contaminated by the prior ink in the apparatus. The fixture consisted of the following elements: (1) a fluid system capable of (a) pressurizing the composition ("ink") in excess of 60 psid (0.41 MPa) thereby producing ink volumetric flow rates of up to about 2 liters/min; (b) delivering pressurized ink to a continuous inkjet printhead drop generator; (c) returning unprinted ink under vacuum to the fluid system ink reservoir; (d) detecting the ink reservoir ink concentration by electrical resistivity measurement and replenishing the ink with inventive Replenisher Fluid R-B (E) if concentrated by water evaporation, and adding more aqueous inkjet ink composition C-C (E) to the ink reservoir instead if it was depleted by use in printing but was at the correct concentration; (e) providing the printhead with inventive Printhead Cleaning and Storage Fluid S-B (E) to flush the nozzles and duct systems in order to restore accurate printing after fouling by dried ink build-up, and to shut down the system for safe storage over significant time durations; (2) a vacuum drum capable of supporting a sheet of porous media (for example, uncoated free sheet paper) or non-porous media (for example, coated or uncoated polymer film) and spinning it continuously at precise speeds synchronized with a control unit to simulate web transport of the printing substrate in roll form; (3) a continuous inkjet printhead PIC box assembly including (a) a KODAK PROSPER Press Jetting Module with a MEMS silicon-based drop generator to form drops of ink and a Coanda gutter to catch non-printing drops when the printer is not printing an image file or when it is not printing a given pixel even if it is printing an image file; (b) a non-printing drop deflection apparatus creating a zone intersecting the drop curtain provided by positive and negative air duct assemblies to direct those drops to the Coanda gutter, and (c) an ink return line to the ink reservoir, and (4) a print controller that (a) controls the printing drum speed and synchronizes the drum location in accord with the data feed to the jetting module and also (b) transmits electrical signals to the jetting module CMOS circuitry that renders a raster processed image into pixel by pixel ink stream stimulation instructions using nozzle plate heater pulse patterns by optimized waveforms to generate non-printing catch drops and printing drops of ink delivered at the printing substrate surface pixel locations, as required.

The fluid system used a Micropump Inc. MICROPUMP series GJ-N23DB380A gear pump to deliver the ink through a Pall Corp. Disposable Filter Assembly capsule filter, DFA4201ZU0045, containing 0.45 µm nominal effective pore size ULTIPOR GF-HV glass fiber media at about 65 psid (0.45 MPa) pressure drop at the nozzle plate, which generated a uniform drop velocity of about 20 m/s. The fluid system gear pump speed setting was continually adjusted to provide and maintain constant fluid pressure at the jetting module to uniformly produce the desired drop velocity as per the system specification. The required system parameter settings for proper jetting and accurate ink replenishment were determined and recorded to a computer file termed an "inkdex" to enable printing on other systems, such as a web press fitted two-up with production KODAK PROSPER S10 Imprinting Systems. The deflected non-printing ink drops were caught on a Coanda gutter and returned to the fluid system ink tank under vacuum. Sustained operation of the printer in catch mode of the non-printing drops resulted in gradual evaporation of the aqueous ink solvent vehicle. Ink concentration was maintained to within about 5% of the original ink concentration by addition of the aqueous pigment-free Replenisher Fluid to the ink, if the latter became more than about 5% concentrated based on an ink electrical resistivity determination. Test targets were raster image processed to produce digital printing signal instructions for each pixel location at the appropriate transport speed of the test substrate at 600×600 pixels per inch (ppi) (236×236 pixels per centimeter (ppcm)) addressability for speeds up to about 1,000 FPM. NewPage STERLING Ultra Gloss paper and/or an uncoated, untreated free sheet paper (for example, International Paper 20-lb (75 g/m$^2$) DATASPEED Laser MOCR) was loaded on to the constant speed, rotating drum, which was synchronized with the print data controller. Various test images were printed at different substrate transport speeds that profiled system functional printing speed capability using a 600-nozzles per inch PROSPER Press Jetting Module in a near-production print-head assembly configuration, which produced a 4.25-inch (10.8 cm) jet curtain print swath. Operational stability and start-up robustness ("runnability") were also probed by printing into a catch pan and assessing time-dependent jet straightness and print raggedness for extended periods, and by conducting multiple shut-down and start-up sequences to assess the time to achieve the first acceptable print and any required interventions [service clean (cross-flush with ink), duct clean (flush with storage fluid), and nozzle plate wipe]. Aqueous inkjet ink composition C-C (E) was found to be runnable and was loaded onto a two-up web press fitted with production KODAK PROSPER S10 Imprinting Systems for long-term testing.

Embodiments according to the present disclosure have been demonstrated above for use in a continuous ink jet printer system that employs a gas flow drop deflection mechanism, thermal drop stimulation devices, and nozzle plates fabricated out of silicon. However, other embodiments according to the present disclosure may also be employed in continuous ink jet printer systems that use electrostatic drop deflection mechanisms, pressure modulation or vibrating body stimulation devices, and nozzles plates fabricated out of other types of materials. Electrostatic deflection may be of the type that includes separate drop charging and drop deflection electrodes or may be of the type that incorporates both functions in a single electrode.

Web components (e.g., nonwoven web materials and film materials) of absorbent articles may be printed with inks formulated according to the description above, and printing may be performed by methods according to the description above. It is contemplated that printing with inks formulated according to the description above, will result in finished product with deposits of dried ink constituting the desired printed graphic elements, wherein the dried ink deposit will have detectable quantities of anti-microbial agents present. It is contemplated that the detectable quantities may be present in the ink deposits to a level of from about 1 to about 1,000 milligrams per square meter (mgsm) web substrate bearing a printed region, or to a level of from about 10 to about 900 mgsm, or to a level of from about 20 to about 800 mgsm, or to a level of from about 30 to about 600 mgsm, or to a level of from about 40 to about 500 mgsm. (For purposes herein, a "printed region" includes any region bearing printing, but the printing does not need to be contiguous or continuous, nor does it need to cover the entirety of the region, to define the printed region. For example, if a substrate has visibly discrete and separate printed graphic elements arranged about the surface of the substrate, any portion of the substrate bearing all or a portion of one or more of the printed graphic elements is a "printed region," and any portion of the substrate that bears no portion of a printed element is an unprinted region. Thus, whether a region is a "printed region," or not, can depend upon the size and/or location of the region being considered.)

It has also been found that printing using ink(s) formulated according to the description above can have lasting anti-microbial effects with respect to the finished product. It has been found that regions printed in ink(s) of such formulation will tend to support less growth of microbes or no growth of microbes, or even have an active antimicrobial/ antibiotic effect, which may be deemed desirable for personal care/personal hygiene products such as diapers, training pants, feminine hygiene products and adult incontinence products. This effect is at least partially reflected in results of application of the Microbiological Susceptibility measurement method described below. Accordingly, use of ink(s) formulated according to the above description for achieving such effect is contemplated.

The present disclosure contemplates (but is not necessarily limited to) at least the following embodiments and combinations thereof, and other combinations of features are contemplated to the extent they may be appreciated by a skilled artisan from the teaching of the present disclosure:

1. An absorbent article comprising a wearer-facing, liquid-permeable topsheet; an outward-facing, liquid impermeable backsheet; and an absorbent core structure disposed between the topsheet and backsheet, wherein a surface of a component material of the article includes a printed region bearing a deposit of an ink composition comprising one or more compounds represented by the following Structure I:

$$HO-CH_2-CH_2-R \qquad (I)$$

wherein R is a substituted or unsubstituted phenyl group or a substituted or unsubstituted phenoxy group.

2. The absorbent article of embodiment 1 wherein the Structure I compound is present in an amount of from about 1 mgsm to about 1,000 mgsm, more preferably from about 10 mgsm to about 900 mgsm, even more preferably from about 20 mgsm to about 800 mgsm, even more preferably from about 30 mgsm to about 600 mgsm, and still more preferably from about 40 mgsm to about 500 mgsm, in the printed region.

3. The absorbent article of either of embodiments 1 or 2 wherein the Bacterial Count Differential at 14 Days of the printed region is greater than the Bacterial Count Differential at 14 Days of an unprinted region of the component material.

4. The absorbent article of either of embodiments 1 or 2 wherein the Bacterial Count Differential at 14 Days of the printed region is greater than the Bacterial Count Differential at 14 Days of an unprinted region of the component material, by at least about 0.3.

5. The absorbent article of either of embodiments 1 or 2 wherein the Bacterial Count Differential at 14 Days of the printed region is greater than the Bacterial Count Differential at 14 Days of an unprinted region of the component material, by at least about 1.0.

6. The absorbent article of either of embodiments 1 or 2 wherein the Bacterial Count Differential at 28 Days of the printed region is greater than the Bacterial Count Differential at 28 Days of an unprinted region of the component material.

7. The absorbent article of either of embodiments 1 or 2 wherein the Bacterial Count Differential at 28 Days of the printed region is greater than the Bacterial Count Differential at 28 Days of an unprinted region of the component material, by at least about 0.3.

8. The absorbent article of any of embodiments 3-5 wherein the Bacterial Count Differential at 28 Days of the printed region is greater than the Bacterial Count Differential at 28 Days of an unprinted region of the component material, by at least about 1.0.

9. An absorbent article product comprising a wearer-facing, liquid-permeable topsheet; an outward-facing, liquid impermeable backsheet; and an absorbent core structure disposed between the topsheet and backsheet, wherein a surface of a component material of the article includes a printed region bearing a deposit of an ink composition comprising one or more compounds represented by the following Structure I:

HO—CH2-CH2-R (I)

wherein R is a substituted or unsubstituted phenyl group or a substituted or unsubstituted phenoxy group;

wherein the Bacterial Count Differential at 14 Days of the printed region is greater than the Bacterial Count Differential at 14 days of an unprinted region of the component material.

10. The absorbent article of embodiment 9 wherein the Bacterial Count Differential at 14 Days of the printed region is greater than the Bacterial Count Differential at 14 Days of an unprinted region of the component material, by at least about 0.3.

11. The absorbent article of embodiment 9 wherein the Bacterial Count Differential at 14 Days of the printed region is greater than the Bacterial Count Differential at 14 Days of an unprinted region of the component material, by at least about 1.0.

12. The absorbent article of embodiment 9 wherein the Bacterial Count Differential at 28 Days of the printed region is greater than the Bacterial Count Differential at 28 Days of an unprinted region of the component material.

13. The absorbent article of embodiment 9 wherein the Bacterial Count Differential at 28 Days of the printed region is greater than the Bacterial Count Differential at 28 Days of an unprinted region of the component material, by at least about 0.3.

14. The absorbent article of embodiment 9 wherein the Bacterial Count Differential at 28 Days of the printed region is greater than the Bacterial Count Differential at 28 Days of an unprinted region of the component material, by at least about 1.0.

15. The absorbent article of any of the preceding embodiments wherein the Structure (I) compound(s) is(are) selected from the group consisting of 2-phenoxyethanol; 2-phenylethanol; ethylene glycol phenyl ether; ethylene glycol monophenyl ether; 1-hydroxy-2-phenoxyethane; phenylethanol; 2-phenylethan-1-ol; phenethyl alcohol; β-hydroxyethylbenzene; β-phenylethanol; benzyl carbinol, and combinations thereof.

16. The absorbent article of any of embodiments 1-15 wherein the deposit comprises a supplemental second antimicrobial agent that is different from the Structure (I) composition.

17. The absorbent article of embodiment 16, wherein the supplemental second antimicrobial agent is selected from the group consisting of iodopropynyl butyl carbamate, piroctone olamine, boric acid, 2,4-dichlorobenzyl alcohol, or a metal ion salt derived from boric acid, or a combination these compounds.

18. The absorbent article of any of the preceding embodiments, wherein the deposit further comprises an anionic polyurethane, an anionic non-aromatic acrylic polymer, an anionic styrene-acrylic polymer, or a combination of two or more of such materials, each of these materials having an acid number of at least 50.

19. The absorbent article of any of the preceding embodiments, wherein the deposit further comprises one or more promoters for the one or more Structure (I) compounds, each of which promoter(s) is an alkane diol having a least 7 carbon atoms and up to and including 12 carbon atoms.

20. The absorbent article of claim 19, wherein the promoter is 1,2-octanediol.

21. The absorbent article of any of the preceding embodiments, wherein R is either an unsubstituted phenyl group or an unsubstituted phenoxy group.

22. The absorbent article of any of the preceding embodiments, wherein the deposit is substantially free of isothiazolinone compounds and formaldehyde-releasing compounds.

23. The absorbent article of embodiment 22 wherein the deposit is substantially free of 2-bromo-2-nitropropane-1,3-diol and/or hexamethylenetetramine chloroallyl chloride.

24. The absorbent article of any of the preceding embodiments, wherein the printed region is comprised by any one or more of a body-facing side of the topsheet, an outward-facing side of the topsheet, a body-facing side of a secondary topsheet disposed between the topsheet and the backsheet, a body-facing side of the backsheet, and an outward-facing surface of the backsheet.

MEASUREMENT METHODS

Organic Compounds of Printing Ink in Graphic Elements Printed on Web Material

Organic compounds of interest in ink, present in areas of web material components of absorbent articles bearing printed graphics, may be detected and quantified using trace-analysis techniques known to one of skill in the art. Accordingly, the following method is to be considered one non-exclusive, optional method that may be used.

A sample of web material of interest including a printed region is excised from the absorbent article in an area quantity specified below. (If the sample section of interest excised from one absorbent article provides an insufficient quantity of material for analysis, corresponding sample sections from additional equivalent absorbent articles may be excised and analyzed together.)

A solvent in which the organic compound of interest is soluble is used to chemically extract the analyte from the sample section. The solvent is then quantitatively analyzed for the organic compound of interest using a technique that is also chemically selective such as GC-MS(/MS) or LC-MS (/MS). (If MS-based techniques are used, a stable-isotope-labeled analyte is typically used as an internal standard.) Based on the measured area of the excised sample section(s) and the volume of solvent used to chemically extract the compound of interest, the concentration of the compound of interest determined to be present in the solvent via quantitative analysis is used to calculate the quantity of compound of interest present per unit surface area of the excised sample section(s). If the compound of interest is detected, the result is a positive detection of the compound of interest, and its level is reported to at least two significant figures in units of milligrams per square meter (mgsm) of the sample section(s).

For example, for analysis of 2-phenoxyethanol (compound of interest) present in a sample of web material having a printed region, a total of 4 cm$^2$ (0.0004 m$^2$) of web material from or including the printed region may be excised from the subject absorbent article(s) and subjected to extraction of the compound of interest via rinsing and agitation in 10 mL of methanol with vortex mixing for approximately 60 minutes. An aliquot of the extract solution is diluted with 75:25 methanol:water, spiked with 2-phenoxyethanol-1,1-d$_2$ internal standard and analyzed by reversed-phase HPLC- MS/MS operated under multiple reaction monitoring (MRM) conditions in positive-ion mode. Neat calibration standards prepared in a 75:25 ratio of MeOH to ultrapure water (resistivity>18.2 MSΩ·cm) are used to quantitate extracted compound of interest. Sample concentrations are determined by back-calculation using a weighted ($1/x^2$) quadratic calibration curve of the peak area ratios generated from neat standards. If the compound of interest is detected, it is reported to be present, and its level is reported to at least two significant figures in mgsm.

Microbiological Susceptibility

The Microbiological Susceptibility Test (MST) Method is used to measure the microbial response associated with a growth medium exposed to a substrate region of interest excised from one or more articles. The method makes use of United States Pharmacopoeia (51) Antimicrobial Effectiveness Testing and more specifically follows the procedures and bacterial challenge of Category 2 products.

A square sample, 1 cm×1 cm, of a component web material having a region of interest is excised aseptically from an absorbent article and transferred into a sterile container. (If the region of interest is smaller than 1 cm×1 cm, smaller samples from corresponding regions of additional equivalent articles constituting 1 cm² surface area in total may be taken and analyzed together.) For example, a region of interest may be a region of web material bearing printed graphic elements, and/or, where a comparative analysis is desired, a region of interest may be a region of component web material having no printing thereon (unprinted region).

*Escherichia coli* (ATTC No. 8739) is used as the challenge organism. The inoculum suspension is prepared according to USP <51> and diluted to the recommended concentration in sterile 0.85% NaCl (w/vol) saline solution. The sample(s) described above is/are placed in a sealed sterile container along with 100 mL of the diluted inoculum. The sealed sterile container containing both the sample(s) and the diluted inoculum is vortexed for 30 seconds. Inoculated samples are stored at 22.5±2.5° C. until sampling for plating.

At the time of sampling for plating and measurement, the contents of the sealed sterile container are stomached in a stomacher (such as the Stomacher 400 Circulator, Seward Ltd., West Sussex, UK, or equivalent) at 260 rpm for 2 minutes. Serial 1:10 dilutions are performed using liquid growth medium (to achieve 1:100, 1:1000 dilutions and so on) as needed to enable a meaningful plate count. Plate counts are performed on 100-mm diameter petri plates, and ideal CFU readings for plates are between 25 and 250. The lowest dilution factor that leads to a raw CFU reading that falls within the allowed range is ideally used to calculate CFU/mL of survivors.

The Starting Bacterial Count is measured immediately after inoculation, with no incubation period, and is defined as the measured concentration (in CFU/mL) for *E. coli*. The Bacterial Count at 14 Days is defined as the measured concentration (in CFU/mL) of *E. coli* survivors at 14 days of incubation. The Bacterial Count at 28 Days is defined as the measured concentration (in CFU/mL) of *E. coli* survivors at 28 days of incubation.

Using the Starting Bacterial Count and the Bacterial Count at 14 Days, the Bacterial Count Differential at 14 Days is defined as $$\text{Bacterial Count Differential at 14 Days} = -\log_{10} \frac{\text{Bacterial Count at 14 Days}}{\text{Starting Bacterial Count}}$$

and is reported to the nearest tenth. Using the Starting Bacterial Count and the Bacterial Count at 28 Days, the Bacterial Count Differential at 28 Days is defined as $$\text{Bacterial Count Differential at 28 Days} = -\log_{10} \frac{\text{Bacterial Count at 28 Days}}{\text{Starting Bacterial Count}}$$

and is reported to the nearest tenth.

The dimensions and/or values disclosed herein are not to be understood as being strictly limited to the exact numerical values recited. Instead, unless otherwise specified, each such dimension or value is intended to mean both the recited value and a functionally equivalent range surrounding that value. For example, a dimension disclosed as "40 mm" is intended to mean "about 40 mm."

Values disclosed herein as ends of ranges are not to be understood as being strictly limited to the exact numerical values recited. Instead, unless otherwise specified, each numerical range is intended to mean both the recited values and any integer values and mixed number values within the range. For example, a range disclosed as "1 to 10" is intended to include 1, 2, 3, 4, 5, 6, 7, 8, 9, and 10, as well as, e.g. and without limitation, 1.012, 2.3, 5.45, 8.391, 9.9999, etc.

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications may be made without departing from the spirit and scope of the invention. It is therefore intended to cover in the appended claims all such changes and modifications that are within the scope of this invention.

What is claimed is:

1. An absorbent article comprising a wearer-facing, liquid-permeable topsheet; an outward-facing, liquid impermeable backsheet; and an absorbent core structure disposed between the topsheet and backsheet, wherein a surface of a component material of the article includes a printed region bearing a deposit of an ink composition comprising one or more compounds represented by the following Structure I:

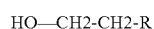   (I)

wherein R is a substituted or unsubstituted phenyl group or a substituted or unsubstituted phenoxy group.

2. The absorbent article of claim 1 wherein the Structure I compound is present in an amount of from about 1 mgsm to about 1,000 mgsm, in the printed region.

3. The absorbent article of claim 2 wherein the Bacterial Count Differential at 14 Days of the printed region is greater than the Bacterial Count Differential at 14 Days of an unprinted region of the component material.

4. The absorbent article of claim 2 wherein the Bacterial Count Differential at 28 Days of the printed region is greater than the Bacterial Count Differential at 28 Days of an unprinted region of the component material.

5. An absorbent article product comprising a wearer-facing, liquid-permeable topsheet; an outward-facing, liquid impermeable backsheet; and an absorbent core structure disposed between the topsheet and backsheet, wherein a surface of a component material of the article includes a printed region bearing a deposit of an ink composition comprising one or more compounds represented by the following Structure I:

$$HO-CH_2-CH_2-R \qquad (I)$$

wherein R is a substituted or unsubstituted phenyl group or a substituted or unsubstituted phenoxy group;

wherein the Bacterial Count Differential at 14 Days of the printed region is greater than the Bacterial Count Differential at 14 days of an unprinted region of the component material.

6. The absorbent article of claim 5 wherein the Bacterial Count Differential at 14 Days of the printed region is greater than the Bacterial Count Differential at 14 Days of an unprinted region of the component material, by at least about 0.3.

7. The absorbent article of claim 5 wherein the Bacterial Count Differential at 14 Days of the printed region is greater than the Bacterial Count Differential at 14 Days of an unprinted region of the component material, by at least about 1.0.

8. The absorbent article of claim 5 wherein the Bacterial Count Differential at 28 Days of the printed region is greater than the Bacterial Count Differential at 28 Days of an unprinted region of the component material.

9. The absorbent article of claim 5 wherein the Bacterial Count Differential at 28 Days of the printed region is greater than the Bacterial Count Differential at 28 Days of an unprinted region of the component material, by at least about 0.3.

10. The absorbent article of claim 5 wherein the Bacterial Count Differential at 28 Days of the printed region is greater than the Bacterial Count Differential at 28 Days of an unprinted region of the component material, by at least about 1.0.

11. The absorbent article product of claim 1 wherein the Structure (I) compound(s) is(are) selected from the group consisting of 2-phenoxyethanol; 2-phenylethanol; ethylene glycol phenyl ether; ethylene glycol monophenyl ether; 1-hydroxy-2-phenoxyethane; phenylethanol; 2-phenylethan-1-ol; phenethyl alcohol; β-hydroxyethylbenzene; β-phenylethanol; benzyl carbinol, and combinations thereof.

12. The absorbent article product of claim 1 wherein the deposit comprises a supplemental second antimicrobial agent that is different from the Structure (I) composition.

13. The absorbent article product of claim 12, wherein the supplemental second antimicrobial agent is selected from the group consisting of iodopropynyl butyl carbamate, piroctone olamine, boric acid, 2,4-dichlorobenzyl alcohol, or a metal ion salt derived from boric acid, or a combination these compounds.

14. The absorbent article product of claim 1, wherein the deposit further comprises an anionic polyurethane, an anionic non-aromatic acrylic polymer, an anionic styrene-acrylic polymer, or a combination of two or more of such materials, each of these materials having an acid number of at least 50.

15. The absorbent article product of claim 1, wherein the deposit further comprises one or more promoters for the one or more Structure (I) compounds, each of which promoter(s) is an alkane diol having a least 7 carbon atoms and up to and including 12 carbon atoms.

16. The absorbent article product of claim 15, wherein the promoter is 1,2-octanediol.

17. The absorbent article product of claim 1, wherein R is either an unsubstituted phenyl group or an unsubstituted phenoxy group.

18. The absorbent article product of claim 1, wherein the deposit is substantially free of isothiazolinone compounds and formaldehyde-releasing compounds.

19. The absorbent article of claim 18 wherein the deposit is substantially free of 2-bromo-2-nitropropane-1,3-diol and/or hexamethylenetetramine chloroallyl chloride.

20. The absorbent article of claim 1, wherein the printed region is comprised by the topsheet.

21. The absorbent article of claim 1, wherein the printed region is comprised by a secondary topsheet disposed between the topsheet and the backsheet.

* * * * *